United States Patent [19]
Li

[11] Patent Number: 5,443,472
[45] Date of Patent: Aug. 22, 1995

[54] MORCELLATOR SYSTEM

[75] Inventor: Lehmann K. Li, Milford, Conn.

[73] Assignee: Li Medical Technologies, Inc., Trumbull, Conn.

[21] Appl. No.: 135,750

[22] Filed: Oct. 13, 1993

Related U.S. Application Data

[63] Continuation-in-part of Ser. No. 134,142, Oct. 8, 1993.

[51] Int. Cl.⁶ .............................................. A61B 17/32
[52] U.S. Cl. ...................................... 606/114; 606/184
[58] Field of Search ........................... 606/1, 106–108, 606/110–114, 127, 128, 166, 167, 170, 171, 184, 185, 205–211

[56] References Cited

U.S. PATENT DOCUMENTS

| | | | |
|---|---|---|---|
| 30,471 | 10/1960 | Dudley | 606/127 |
| 3,314,431 | 4/1967 | Smith | 606/108 |
| 5,147,371 | 9/1992 | Washington | 606/110 |
| 5,190,555 | 3/1993 | Wetter | 606/114 |
| 5,190,561 | 3/1993 | Graber | 606/114 |
| 5,201,740 | 4/1993 | Nakao et al. | 606/110 |
| 5,215,521 | 6/1993 | Cochran et al. | 606/128 |

FOREIGN PATENT DOCUMENTS

| | | | |
|---|---|---|---|
| 0499243 | 8/1992 | European Pat. Off. | 606/114 |
| 1706582 | 1/1992 | U.S.S.R. | 606/106 |

*Primary Examiner*—Stephen C. Pellegrino
*Assistant Examiner*—Glenn Dawson
*Attorney, Agent, or Firm*—Pandiscio & Pandiscio

[57] ABSTRACT

A morcellator system for use in removing relatively large pieces of tissue from the body during laparoscopic surgery. The system generally comprises a morcellator device for dissecting a large piece of tissue into smaller pieces of tissue and extracting them from the surgical site, and a tissue containment device for capturing the large piece of tissue and immobilizing it so that it may be dissected by the morcellator.

16 Claims, 19 Drawing Sheets

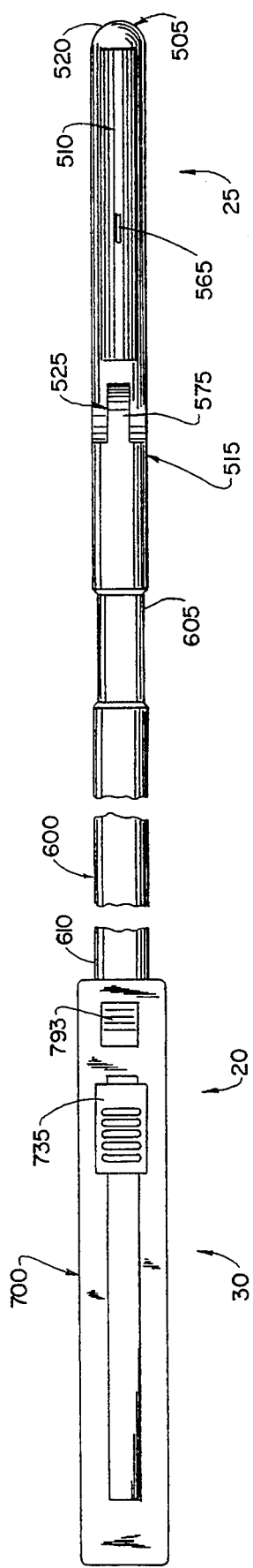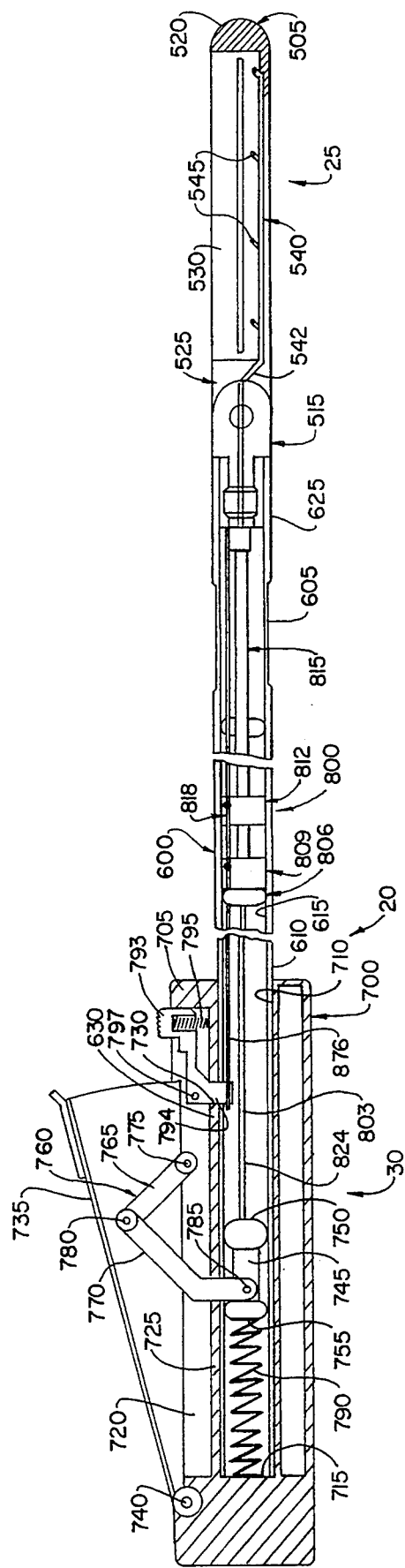

MORCELLATOR SYSTEM

This application is a continuation-in-part of my prior U.S. patent application Ser. No. 08/134,142, filed Oct. 8, 1993.

FIELD OF THE INVENTION

This invention relates to laparoscopic surgery in general, and more particularly to apparatus and methods for removing severed tissue from the body during such surgery.

BACKGROUND OF THE INVENTION

In laparoscopic surgery, access is gained to an interior surgical site by making one or more small incisions in the body which extend down to the interior surgical site, and then inserting a hollow tube or cannula into each incision so that the cannulas can act as liners to hold the incisions open and thereby provide portals leading down to the interior surgical site. A laparoscopic procedure can then be performed by passing surgical instruments (e.g. cutting devices, clamps, viewing apparatus, etc.) down the cannulas so that the distal working ends of the instruments can be positioned and used about the surgical site, while the proximal handle ends of the instruments remain outside the body where they can be grasped by the surgeon.

Laparoscopic procedures frequently involve the removal of tissue from the interior surgical site. For example, one of the most common laparoscopic procedures practiced today is the laparoscopic cholecystectomy, in which the patient's gallbladder is removed from the body. In other laparoscopic procedures, other tissue (e.g. an appendix, portions of the intestine, etc.) may be removed from the body. In some situations, the excised tissue is relatively small and can be passed through the narrow cannula opening intact. In other situations, however, the excised tissue is too large to fit through a cannula intact. When this occurs, the excised tissue must generally be cut down into a number of smaller pieces before it can be passed through a cannula. For example, in many laparoscopic cholecystectomies, the patient's gallbladder must be dissected into several smaller pieces before it can be removed through a cannula.

Such dissection of the excised tissue can present problems for the surgeon. For one thing, the excised tissue must generally be held in place by one instrument (e.g. a forceps) while it is dissected into several smaller pieces by another instrument (e.g. a cutting tool). These smaller pieces of tissue must themselves be captured by apparatus so that they can be removed from the body. It can be difficult to coordinate the holding, dissecting and capturing of the various pieces of tissue, particularly during laparoscopic surgical procedures where visibility is generally limited and tissue access restricted.

OBJECTS OF THE INVENTION

Accordingly, the principal object of the present invention is to provide apparatus and methods for use in removing tissue from the body during laparoscopic procedures.

Another object of the present invention is to provide a morcellator system for use in laparoscopically dissecting a relatively large piece of tissue while it is located at an interior surgical site, and then removing the resulting smaller pieces of tissue from the body.

Still another object of the present invention is to provide a morcellator device for use in dissecting a relatively large piece of tissue into a number of smaller pieces during a laparoscopic surgical procedure.

Yet another object of the present invention is to provide a morcellator device for use in dissecting a relatively large piece of tissue into a number of smaller pieces during a laparoscopic surgical procedure, wherein the morcellator includes means for capturing those smaller pieces of tissue to the morcellator until the morcellator is removed from the body.

And another object of the present invention is to provide a tissue containment device for use in capturing a relatively large piece of tissue during a laparoscopic surgical procedure.

Still another object of the present invention is to provide a tissue containment device for use in capturing a relatively large piece of tissue during a laparoscopic surgical procedure, wherein the tissue containment device is adapted to be used in conjunction with a morcellator device to form a morcellator system for laparoscopically capturing and dissecting a relatively large piece of tissue while it is located at an interior surgical site and then removing the resulting smaller pieces of tissue from the body, and further wherein the tissue containment device is capable of progressively closing down in size so as to keep the relatively large piece of tissue captured to the tissue containment device even as that piece of tissue is being reduced in size by the morcellator.

Yet another object of the present invention is to provide a morcellator system for use in dissecting a relatively large piece of tissue while it is located at a surgical site and then removing the resulting smaller pieces of tissue from the surgical site, wherein the morcellator system is adapted for use in both laparoscopic and open surgeries.

SUMMARY OF THE INVENTION

These and other objects are addressed by the present invention, which comprises a morcellator system for use in removing relatively large pieces of tissue from the body during laparoscopic surgery. The morcellator system generally comprises a morcellator device and a tissue containment device.

The morcellator device generally comprises an outer tube having a distal end terminating in a distal end surface, a proximal end, an internal passageway extending between the distal end and the proximal end, and an opening formed in the distal end at a location proximal to the distal end surface and communicating with the interior passageway. The morcellator also comprises an inner tube having a distal end terminating in a distal end surface, a proximal end, and an interior passageway extending between the distal end and the proximal end, with the inner tube being sized and disposed so as to make a close sliding fit within the outer tube.

The morcellator also comprises a handle assembly comprising a body and actuating means, with the proximal end of the outer tube being attached to the body and with the proximal end of the inner tube being attached to the actuating means. The actuating means are adapted to move the inner tube between (1) a first distal position wherein the opening formed in the outer tube is closed off by the inner tube, and (2) a second proximal position wherein the opening formed in the outer tube is at least part way open.

The morcellator also comprises first tissue holding means connected to the inner tube and projecting into the interior of the inner tube so as to permit tissue to move proximally through the inner tube and to prevent tissue from moving distally through the inner tube. The morcellator also comprises second tissue holding means connected to the outer tube and projecting into the interior of the outer tube so as to permit tissue to move proximally through the outer tube and to prevent tissue from moving distally through the outer tube.

In use, the morcellator's actuating means are first used so as to place the inner tube into its aforementioned first position. With the morcellator's distal opening thus closed, the distal end of the morcellator is placed next to a relatively large tissue mass which is to be dissected. Then the actuating means are actuated so as to draw the inner tube proximally into its aforementioned second position and thereby open up the morcellator's distal opening. Next, the morcellator is moved against the tissue mass so that a portion of the tissue mass enters the morcellator's distal opening. Then the actuating means are actuated again so as to place the inner tube back into its aforementioned first position, thereby closing the morcellator's distal opening. This will sever a small piece of tissue from the tissue mass, with the severed piece of tissue being contained within the distal end of the morcellator's inner tube. Next, the actuating means are used to place the inner tube back into its aforementioned second position. As the inner tube moves backward, the first tissue holding means hold the severed tissue to the inner tube so that the severed piece of tissue is carried proximally with the inner tube and thus engages the second tissue holding means. Then the distal end of the morcellator is moved against the tissue mass again so that another portion of the tissue mass enters the morcellator's now-open distal opening. Then the actuating means are actuated again so as to place the inner tube back into its aforementioned first position. As this occurs, the piece of tissue previously severed is held in place by the second tissue holding means so that the severed piece of tissue does not move distally with the inner tube. As the inner tube reaches it's aforementioned first position, the morcellator's distal opening is once again closed. This will sever another small piece of tissue from the tissue mass, with that small piece of tissue being contained within the distal end of the morcellator's inner tube. The foregoing process is then repeated as necessary so as to properly dissect the desired tissue mass, with the severed pieces of tissue being contained within the morcellator's inner tube.

The tissue containment device generally comprises a shaft having a distal end, a proximal end, and an interior passageway extending between the distal end and the proximal end. The tissue containment device also comprises a cylindrical body releasably connected to the distal end of the shaft, with the cylindrical body itself comprising a distal end, a proximal end and an interior passageway extending between the distal end and the proximal end, and further comprising at least one manifold element located within the interior passageway and adapted to guide closure means.

The tissue containment device also comprises containment means deployable from the cylindrical body, the containment means comprising a flexible, generally cylindrical bag or net or other containment element, at least one substantially rigid, longitudinally-extending spar connected to the flexible, generally cylindrical bag or net or other containment element, a plurality of openings formed in the spar, and closure means extending out of the at least one manifold and through the plurality of openings formed in the spar.

The tissue containment device also comprises a handle assembly. Release means are also provided for permitting the containment means to be moved from (1) a first fully retracted position wherein the bag or net or other containment element is substantially fully withdrawn into the cylindrical body's interior passageway, and (2) a second fully deployed position wherein the bag or net or other containment element is substantially fully extended out of the cylindrical body's interior passageway. The tissue containment device also comprises retracting means connected to the closure means and adapted to move the containment means from (2) the aforementioned second fully deployed position wherein the bag or net or other containment element is substantially fully extended out of the cylindrical body's interior passageway, and (3) a third intermediate position wherein the bag or net or other containment element is partially withdrawn into the cylindrical body's interior passageway. The retracting means are adapted so that they can progressively withdraw the bag or net or other containment element further and further into the cylindrical body's interior passageway, as desired, in order to reduce the interior volume of the containment means.

In use, the tissue containment device initially has its containment means placed into their aforementioned first retracted position. Then the distal end of the tissue containment device is placed near to the tissue mass which is to be captured. Next, the release means are manipulated so that the containment means may be moved from their aforementioned first retracted position into their aforementioned second fully deployed position. Then the tissue containment device and/or the tissue mass is/are maneuvered so that the tissue mass enters the containment means. Next, the retracting means are used to move the containment means from their aforementioned second fully deployed position into their aforementioned third intermediate position, wherein the containment means will be partially withdrawn into the cylindrical body's interior passageway and the tissue mass will be securely captured to the tissue containment device. The retracting means may thereafter be activated further as desired so as to progressively withdraw the containment means further and further into the cylindrical body's interior passageway, thereby drawing the captured tissue mass closer and closer to the device's cylindrical body.

Preferably the aforementioned morcellator and the aforementioned tissue containment device are used in conjunction with one another, so as to together capture and then dissect a relatively large tissue mass into several smaller pieces of tissue with the severed pieces of tissue being contained within the morcellator's inner tube. In such an arrangement, the distal end of the morcellator might be placed into the tissue containment device's deployed containment means along with the tissue mass, with the containment means being continually retracted into the tissue containment device so as to keep the tissue mass under control and adjacent to the morcellator's opening and closing distal opening.

BRIEF DESCRIPTION OF THE DRAWINGS

Still other objects and features of the present invention will be more fully disclosed or rendered obvious by the following detailed description of the preferred embodiments of the invention, which are to be considered together with the accompanying drawings wherein like numbers refer to like parts and further wherein:

FIG. 10 is a top view of the tissue containment device;

FIG. 11 is a side view in section of the tissue containment device, with the containment means having been omitted from the drawing in order to show additional detail;

DETAILED DESCRIPTION OF THE PREFERRED EMBODIMENTS

Figure 1:
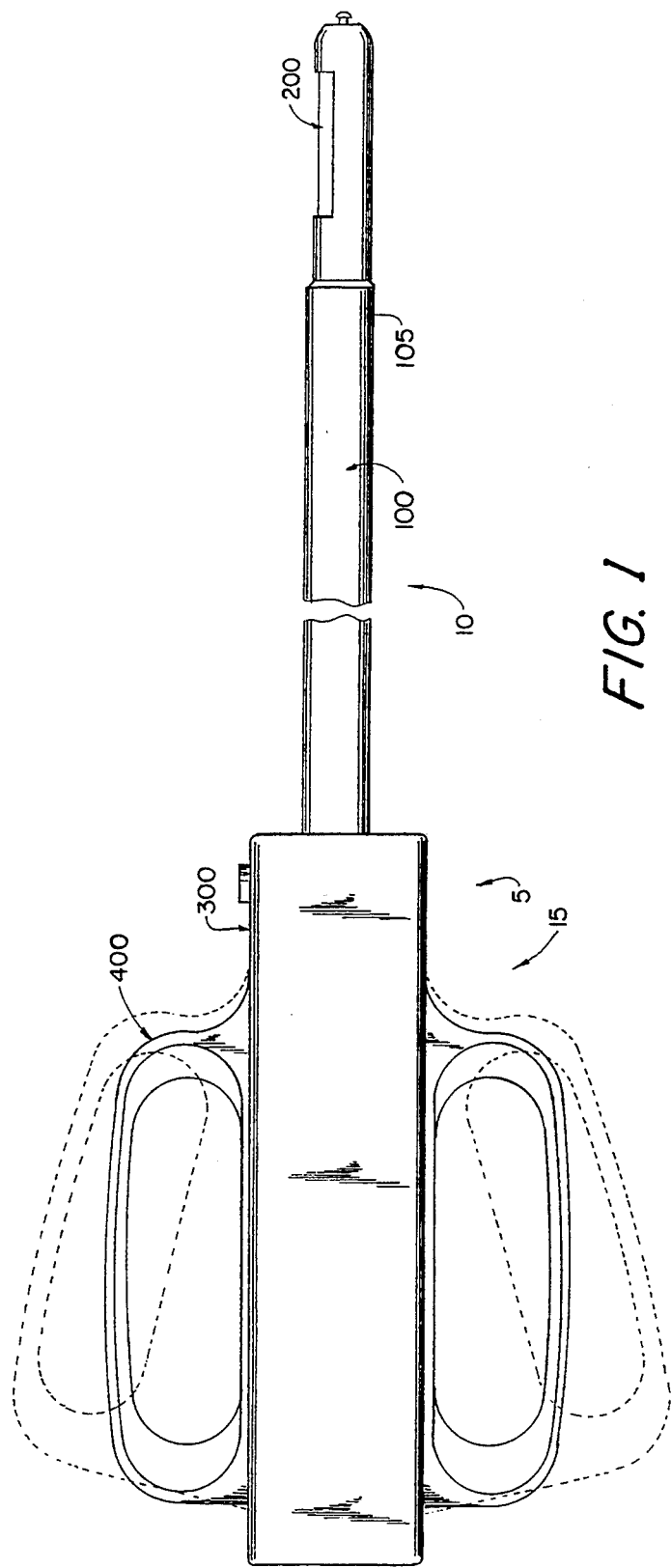
FIG. 1 is a side view of a morcellator device formed in accordance with the present invention.

The present invention comprises a morcellator system for use in removing relatively large pieces of tissue from the body during laparoscopic surgery. The morcellator system generally comprises a morcellator device 5 comprising a cutting assembly 10 and a handle assembly 15 (FIGS. 1–8 and 23–28) and a tissue containment device 20 comprising a tissue containment assembly 25 and a handle assembly 30 (FIGS. 9–28).

More particularly, and looking now at FIGS. 1–8, morcellator 5 generally comprises the cutting assembly 10 which in turn comprises an outer tube 100 and an inner tube 200, and the handle assembly 15 which in turn comprises fixed handle means 300 and movable handle means 400.

Figure 3:
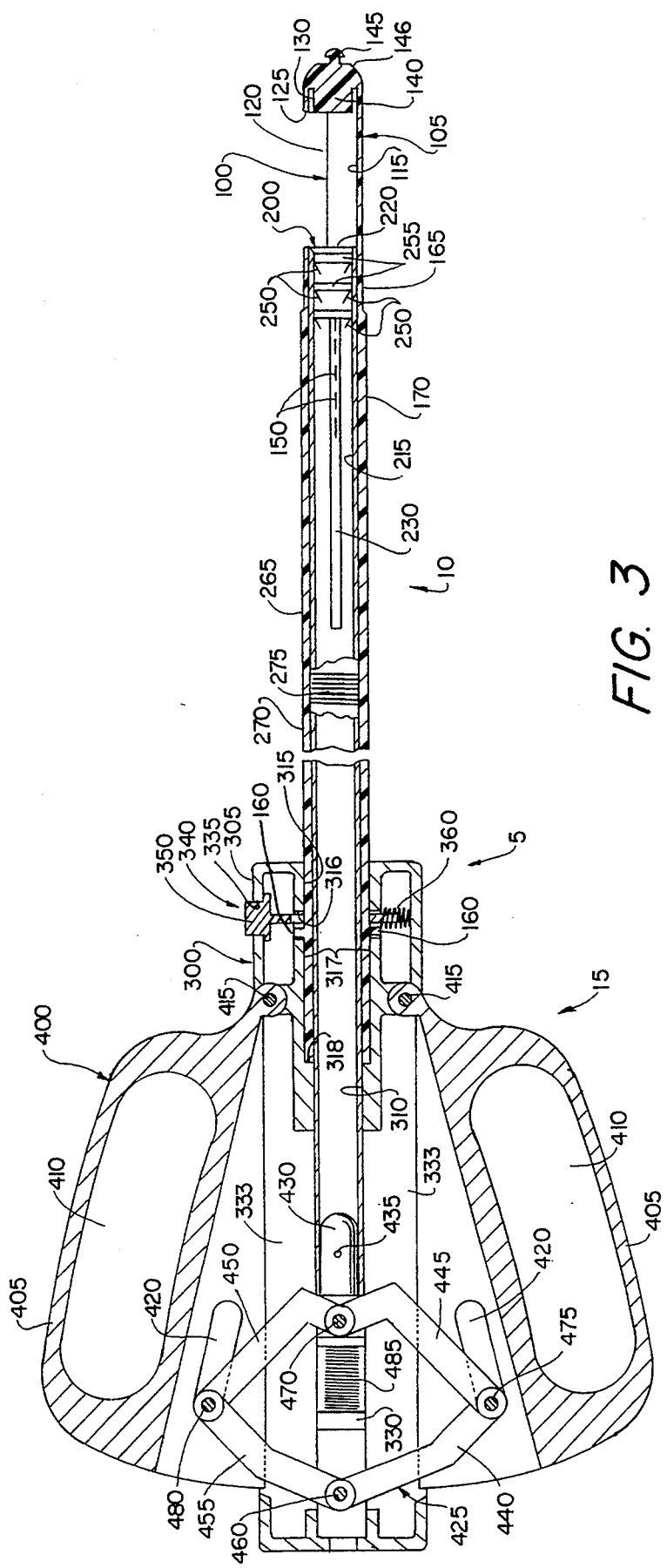
FIG. 3 is a side view in section of the morcellator.
Figure 4:
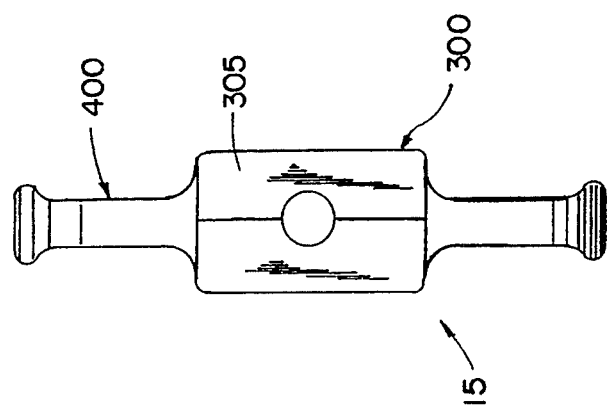
FIG. 4 is a front view of the morcellator.
Figure 5:
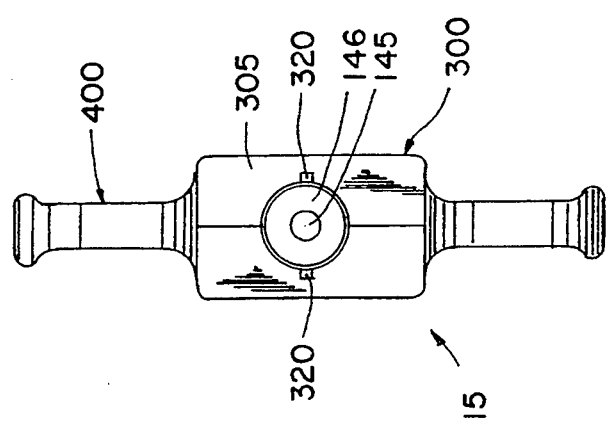
FIG. 5 is a rear view of the morcellator.

Turning first to cutting assembly 10, outer tube 100 generally comprises a distal end 105 (FIGS. 1 and 6), a proximal end 110 (FIG. 6), and an interior passageway 115 (FIG. 3). A rectangular distal opening 120 (FIGS. 1, 6 and 7) is formed in the distal end of outer tube 100. A sharp cutting edge 125 (FIGS. 3,6 and 7) is provided at the distal end of opening 120. An annular groove 130 (FIG. 3) is formed in the distal end of outer tube 100. Annular groove 130 starts approximately flush with sharp cutting edge 125 and extends distally thereof. Annular groove 130 defines a cylindrical plug 140 (FIG. 3). A front knob 145 (FIGS. 3, 6 and 7) is disposed on the outer tube's distal end surface 146.

A plurality of barb-receiving bores 147 (FIG. 7) extend through the side wall of outer tube 100. Bores 147 are arranged in two diametrically-opposed rows, one on each side of outer tube 100. Tissue barbs 150 (FIGS. 3 and 7) are disposed in bores 147 so that they form two diametrically-opposed rows of barbs. Barbs 150 are securely fixed in bores 147. Barbs 150 are arranged so that they extend inwardly and proximally from the wall of outer tube 100 so as to project significantly into the interior of outer tube 100. Barbs 150 are formed out of a relatively strong and resilient material, e.g. spring steel.

Outer tube 100 also comprises an annular proximal end surface 155 (FIG. 8), and two diametrically-opposed locking pins 160 (FIGS. 3,6 and 8) which extend outwardly from the outer surface of tube 100.

Outer tube 100 is preferably (but not necessarily) formed with a two-part construction, i.e., it is preferably formed out of a metal shaft portion 165 (FIG. 3) and a plastic shaft portion 170 (FIG. 3). In the preferred embodiment of the invention, plastic shaft portion 170 is substantially permanently joined to metal shaft portion 165, e.g. during molding. In addition, plastic shaft portion 170 is preferably formed out of a clear plastic material so that the surgeon can visually observe any materials contained within the plastic shaft portion 170.

Figure 6:
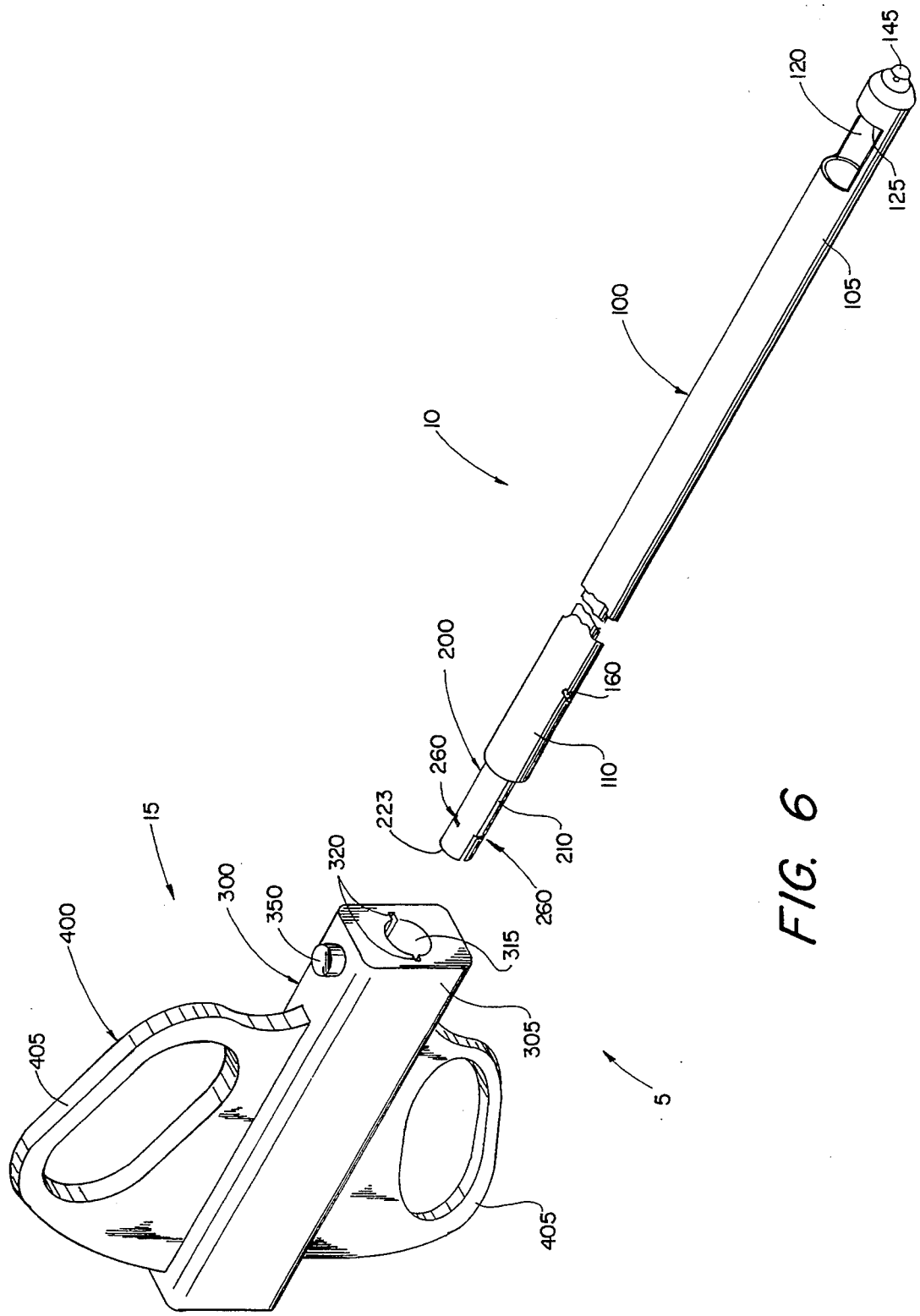
FIG. 6 is a perspective view of the morcellator, wherein the morcellator's cutting assembly is shown in telescoping relation to the morcellator's handle assembly.

The morcellator's cutting assembly 10 also comprises an inner tube 200. Inner tube 200 generally comprises a distal end 205 (FIG. 7), a proximal end 210 (FIG. 6), and an interior passageway 215 (FIG. 3). Inner tube 200 terminates in an annular distal end surface 220 (FIG. 3), and in a substantially annular proximal end surface 223 (FIGS. 6 and 8). A sharp cutting edge 225 (FIG. 7) is disposed along at least a portion of distal end surface 220. Two diametrically-opposed, longitudinally-extending slots 230 (FIGS. 3 and 7) are formed in the side wall of inner tube 200. Slots 230 are spaced from, and do not intersect, annular distal end surface 220. Slots 230 serve to permit the outer tube's barbs 150 to project through the inner tube's side wall so as to engage tissue contained within the interior of inner tube 200, as will hereinafter be disclosed in further detail.

Figure 7:
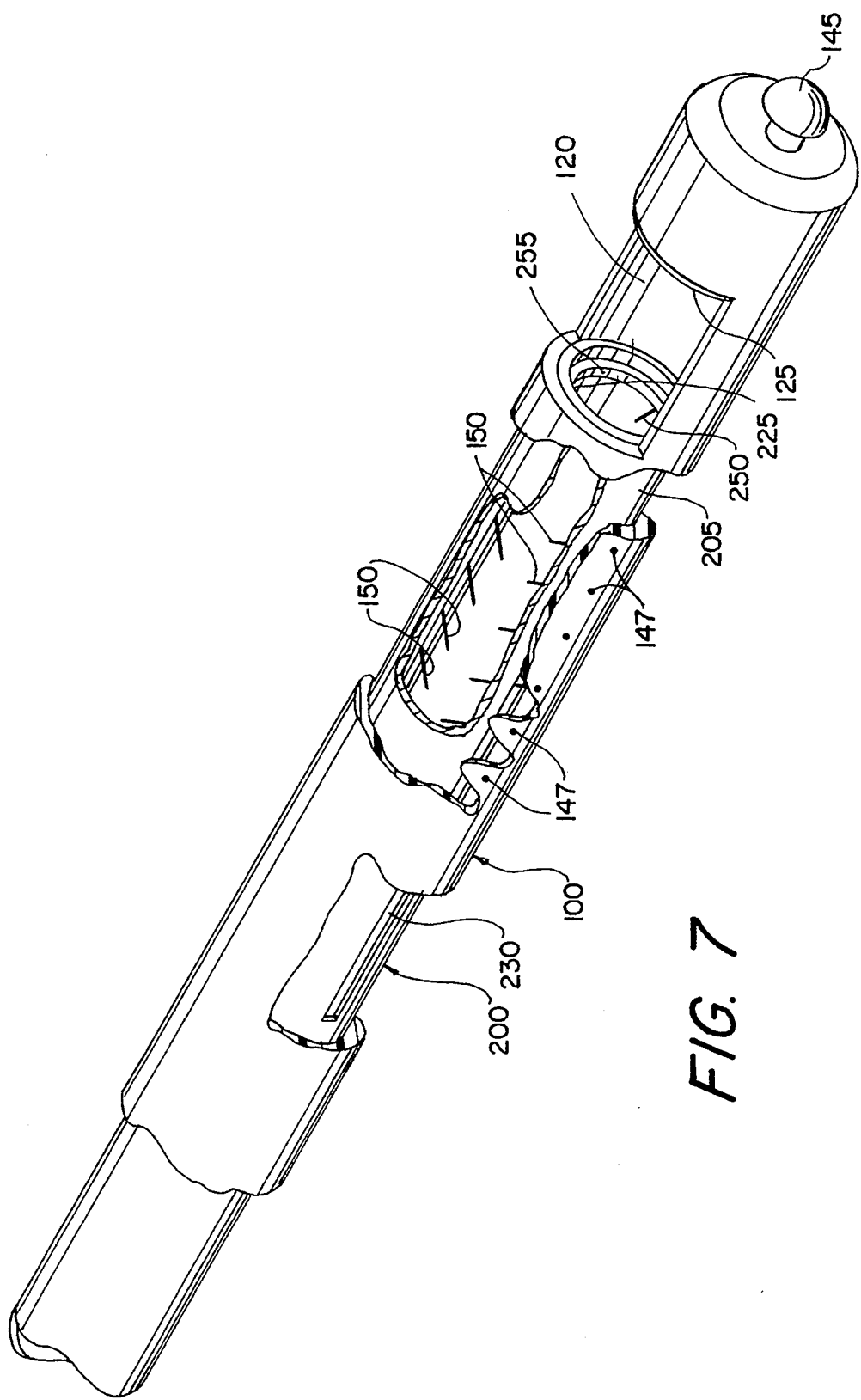
FIG. 7 is a perspective view showing the distal end of the morcellator's cutting assembly, with portions of the assembly's tube members being broken away.
Figure 8:
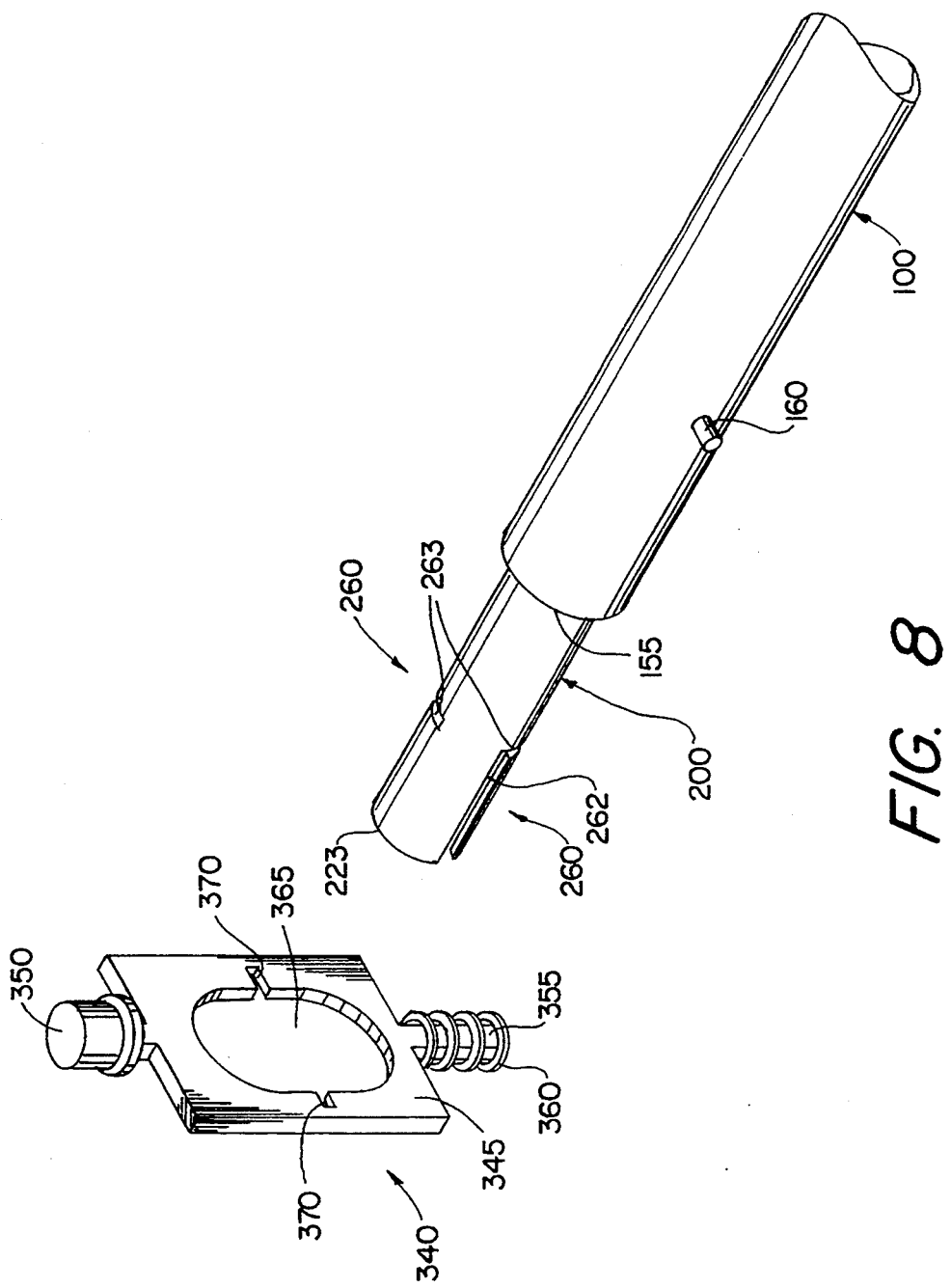
FIG. 8 is a perspective view showing the handle assembly's gate subassembly and the proximal end of the cutting assembly in telescoping relation to one another.
Figure 9:
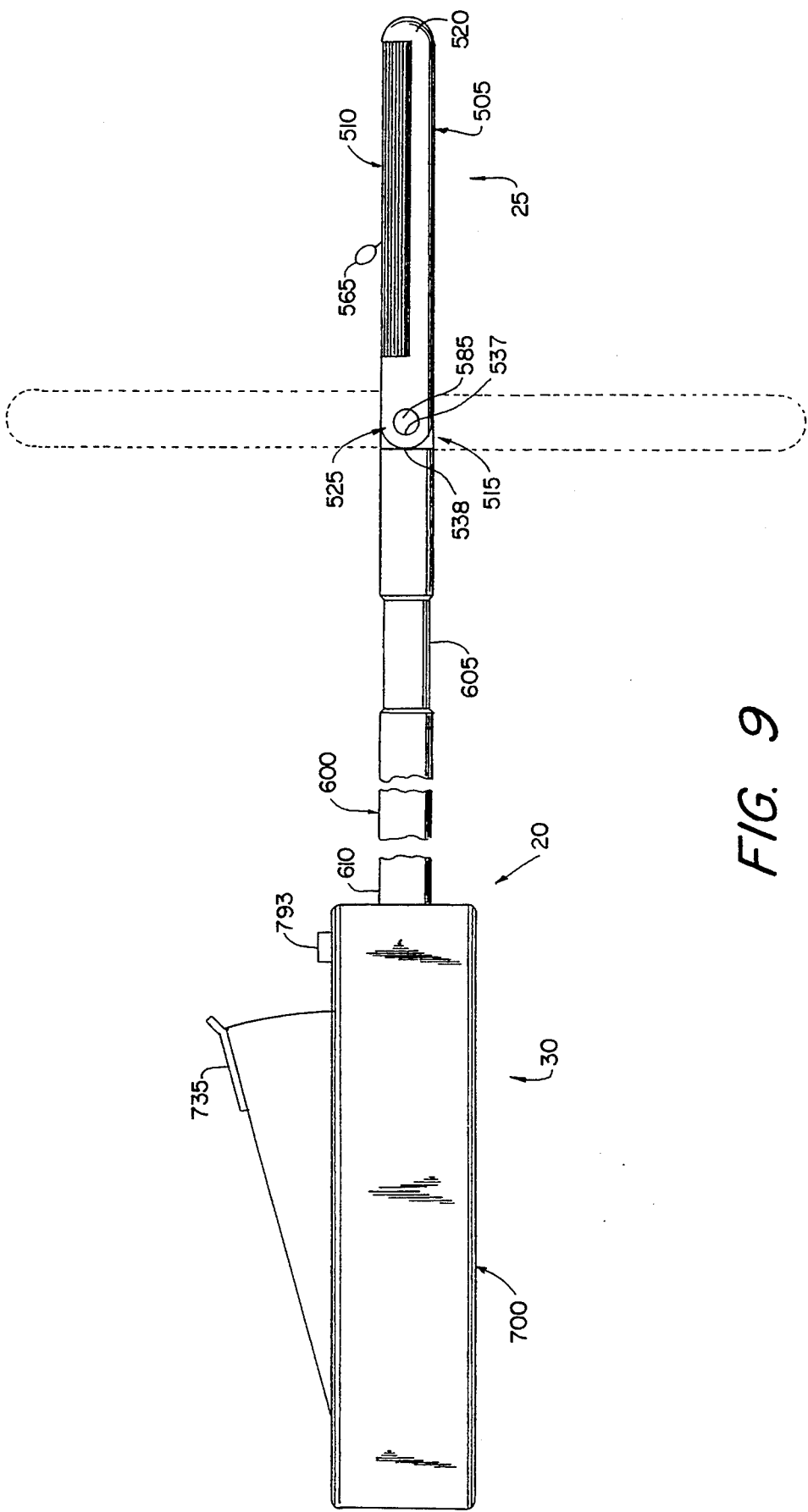
FIG. 9 is a side view of a tissue containment device formed in accordance with the present invention.
Figure 13:
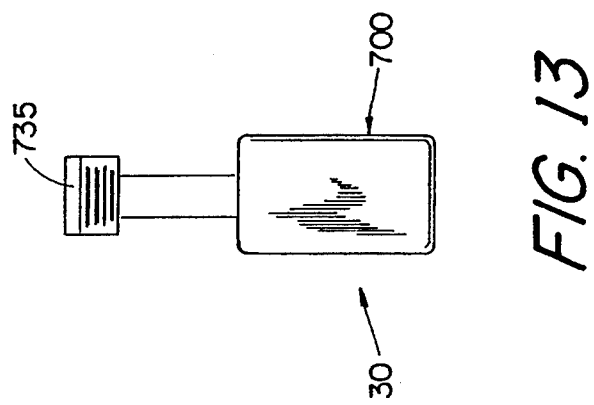
FIG. 13 is a rear view of the tissue containment device.
Figure 12:
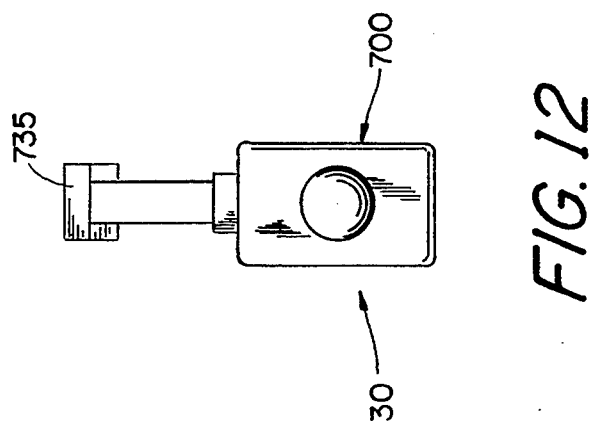
FIG. 12 is a front view of a portion of the tissue containment device's handle assembly.

Inner tube 200 also comprises a plurality of tissue barbs 250 (FIGS. 3 and 7). Barbs 250 are fixed to a plurality of rings 255 (FIGS. 3 and 7) which are themselves attached to the inside of inner tube 200, whereby barbs 250 are securely attached to inner tube 200. Preferably two barbs 250 are attached to each ring 255, with the two barbs being disposed in diametrically-opposed relation to one another. In any case, barbs 250 are arranged in a pair of diametrically-opposed rows, with one row on the top of tube 200 and one row on the bottom of tube 200 (FIGS. 3 and 7). Barbs 250 are arranged so that they extend inwardly and proximally from the wall of inner tube 200 so as to project significantly into the interior of inner tube 200. Barbs 250 are formed out of a relatively strong and resilient material, e.g. spring steel.

A pair of diametrically-opposed, L-shaped slots 260 (FIGS. 6 and 8) are formed at the proximal end of inner tube 200. Each of the L-shaped slots 260 comprises a longitudinally-extending portion 262 (FIG. 8) and a circumferentially-extending portion 263 (FIG. 8). The longitudinally-extending portions 262 open on the tube's substantially annular proximal end surface 223. L-shaped slots 260 permit inner tube 200 to be connected to portions of handle assembly 15, as will hereinafter be disclosed in further detail.

Inner tube 200 is preferably (but not necessarily) formed with a two-part construction, i.e., it is preferably formed out of a metal shaft portion 265 (FIG. 3) and a plastic shaft portion 270 (FIG. 3). In the preferred embodiment of the invention, metal shaft portion 265 is joined to plastic shaft portion 270 by a screw arrangement 275 (FIG. 3). In addition, plastic shaft portion 270 is preferably formed out of a clear plastic material so that the surgeon can visually observe any materials contained within the plastic shaft portion 270.

Outer tube 100 and inner tube 200 together form the cutting assembly 10. To this end, outer tube 100 and inner tube 200 are sized so that inner tube 200 may be telescopically inserted into and make a close sliding fit within outer tube 100 (FIGS. 3, 6, 7 and 8). Outer tube 100 and inner tube 200 are sized so that the proximal end of the inner tube will protrude out of the proximal end of the outer tube (with the L-shaped slots 260 completely exposed) when the inner tube's distal end surface 220 bottoms out in the outer tube's annular groove 130. In addition, outer tube 100 and inner tube 200 are sized so that the outer tube's barbs 150 will ride in the inner tube's side wall slots 230 as the inner tube reciprocates between (i) a first position in which the inner tube's distal end surface 220 bottoms out in the outer tube's annular groove 130, and (ii) a second position in which the inner tube's distal end surface 220 is disposed on the proximal side of the outer tube's rectangular distal opening 120 (i.e., in the position shown in FIG. 3).

From the standpoint of assembly, it is to be appreciated that cutting assembly 10 is assembled by first securely attaching barbs 250 to inner tube 200, then passing inner tube 200 into outer tube 100 so that the inner tube's side wall slots 230 are aligned with the outer tube's bores 147, then positioning the outer tube's barbs 150 in the outer tube's bores 147 and into the inner tube's side wall slots 230, and finally securely fixing barbs 150 in bores 147. In this way the outer tube's barbs 150 and the inner tube's barbs 250 will both project into the interior of inner tube 200.

Turning next to handle assembly 15, fixed handle means 300 generally comprises a body 305 (FIGS. 3-6) having a central bore 310 (FIG. 3) and a front counterbore 315 (FIGS. 3 and 6). An opening 316 (FIG. 3) intersects front counterbore 315 so as to define a housing wall 317 (FIG. 3) which extends about the perimeter of counterbore 315. Central bore 310 and front counterbore 315 together define an annular shoulder 318 (FIG. 3) at their intersection. A pair of diametrically-opposed side slots 320 (FIGS. 4 and 6) extend proximally into body 305 and communicate with front counterbore 315.

Body 305 also comprises a laterally extending wall 330 (FIG. 3), top and bottom slots 333 (FIG. 3), and a top opening 335 (FIG. 3). Top opening 335 is aligned with housing opening 316, as will hereinafter be described in further detail.

Fixed handle means 300 also comprise a gate assembly 340 (FIGS. 3 and 8). Gate assembly 340 in turn comprises a planar body 345. A top button 350 (FIG. 3, 6 and 8) extends out of the top end of planar body 345, and a bottom post 355 (FIG. 8) extends out of the bottom end of planar body 345. A spring 360 (FIGS. 3 and 8) is positioned about, and extends downward from, bottom post 355. An elliptical opening 365 (FIG. 8) is formed in the central portion of planar body 345. Two diametrically-opposed side slots 370 (FIG. 8) communicate with eliptical opening 365. Gate assembly 340 is positioned within housing 305 so that the gate assembly's planar body 345 extends through housing opening 316, with spring 360 biasing the planar body in an upward direction so that top button 350 protrudes out of housing body 305 (FIG. 3), and so that the gate assembly's side slots 370 normally are not aligned with housing slots 320. However, it will also be appreciated that the gate assembly's side slots 370 can be selectively aligned with housing slots 320 by appropriately pressing downward on the gate assembly's top button 350.

Movable handle means 400 generally comprise two handle members 405 (FIGS. 3 and 6). Each of the handle members 405 in turn comprises a finger-receiving opening 410 (FIG. 3), a mounting pin 415 for mounting that handle member to body 305 (FIG. 3), and a camming slot 420 for connecting that handle member to the remainder of movable handle means 400 (FIG. 3).

Movable handle means 400 also comprises a linkage assembly 425 (FIG. 3). Linkage assembly 425 generally comprises a front plug 430 (FIG. 3) adapted to be partially inserted into the interior of inner tube 200 as will hereinafter be described in further detail, and a pair of diametrically-opposed locking pins 435 (FIG. 3) which extend laterally outward from front plug 430. Locking pins 435 serve to secure front plug 430 to inner tube 200, as will hereinafter also be described in further detail. In addition, linkage assembly 425 also comprises four links 440, 445, 450, and 455 (FIG. 3). Links 440 and 455 are pinned to one another and to the fixed housing 305 by a pin 460 (FIG. 3). Links 445 and 450 are pinned to one another and to the movable plug 430 by a pin 470 (FIG. 3). Links 440 and 445 are pinned to each other and to one of the camming slots 420 by a pin 475 (FIG. 3). Links 450 and 455 are pinned to each other and to the other of the camming slots 420 by a pin 480 (FIG. 3). A coiled compression spring 485 (FIG. 3) is positioned between fixed housing wall 330 and the proximal end of the movable plug 430 so as to bias plug 430 away from housing wall 330. Thus it will be seen that spring 485 normally biases plug 430 distally, and hence handle members 405 together, so that the handle members will normally assume the position shown in FIG. 1. At the same time, however, it is also to be appreciated that the user can overcome that bias and urge the front plug 430 proximally by pulling handle members 405 apart, in the manner shown in FIG. 3 (and in phantom in FIG. 1).

The assembled cutting assembly 10 is attached to the assembled handle assembly 15 as follows. First, the proximal ends of the assembled tubes 100 and 200 are passed into the housing assembly's front counterbore 315 so that the diametrically-opposed locking pins 160 on outer tube 100 (FIGS. 6 and 8) pass into the two corresponding side slots 320 (FIGS. 4 and 6) on fixed handle member 305. As the assembled tubes 100 and 200 are passed rearwardly through fixed handle member 305 and into the gate assembly's elliptical opening 365, top button 315 (FIGS. 3, 6 and 8) is depressed so as to force the gate assembly's planar body 345 (FIG. 8) downward against the power of spring 360 (FIGS. 3 and 8). This will bring the gate assembly's side slots 370 (FIG. 8) downward into alignment with the handle member's two side slots 320, and hence into alignment with the outer tube's two locking pins 160 which are disposed in the housing member's two side slots 320. This will allow the outer tube's two diametrically-opposed locking pins 160 to slip through gate assembly 340. The assembled tubes 100 and 200 are then pushed further rearward through elliptical opening 365 until the outer tube's annular proximal end surface 155 (FIG. 8) engages the handle's annular shoulder 318 (FIG. 3). This will halt rearward movement of cutting assembly 10. As this occurs, the front plug's two diametrically-opposed locking pins 435 (FIG. 3) enter the two longitudinally-extending portions 262 (FIG. 8) of L-shaped slots 260 and come to rest adjacent to the circumferentially-extending portions 263 (FIG. 8). Next, the cutting assembly 10 is rotated 90 degrees so that (i) the front plug's two diametrically-opposed locking pins 435 (FIG. 3) are driven into the two circumferentially-extending portions 263 (FIG. 8) of L-shaped slots 260, thus locking inner tube 200 to front plug 430, and (ii) the outer tube's two diametrically-opposed locking pins 160 (FIGS. 3, 6 and 8) are placed into a close sliding engagement with portion 317 (FIG. 3) of housing 305 and the proximal surface of planar body 345. This will securely lock outer tube 100 to the fixed housing 305, and the inner tube 200 to the movable front plug 430.

Figure 2:
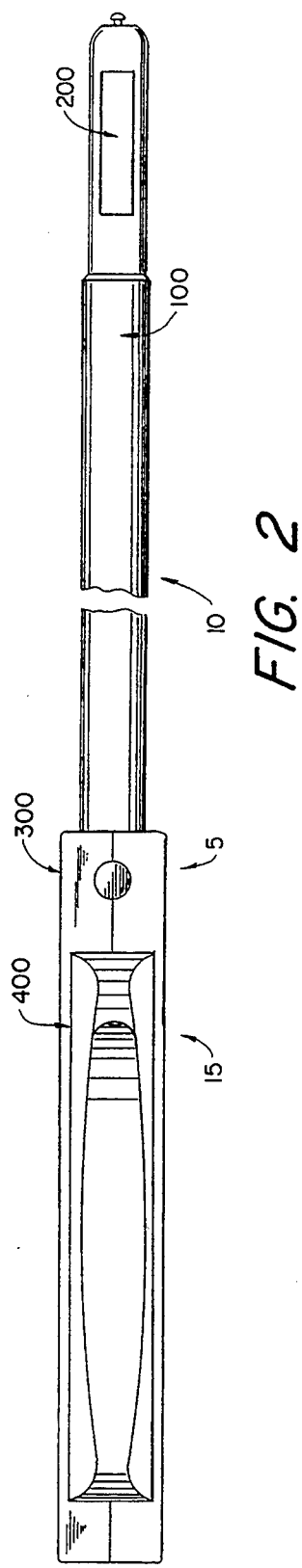
FIG. 2 is a top view of the morcellator.

As a result of this construction, it will be seen that spring 485 (FIG. 3) normally biases inner tube 200 forward relative to outer tube 100 so that inner tube 200 bottoms out in annular groove 130 (FIG. 3) and the outer tube's rectangular distal opening 120 is closed off by inner tube 200 (FIGS. 1 and 2). In this position handle members 405 will be drawn inboard, into the position shown in FIG. 1. At the same time, however, pulling handle members 405 apart will cause inner tube 200 to retreat relative to outer tube 100, so that the outer tube's rectangular distal opening 120 will be opened up, in the manner shown in FIGS. 3 and 6.

It is to be noted that cutting assembly 10 may be dismounted from handle assembly 15 after use. This is done by essentially reversing the aforementioned mounting process, i.e., by first rotating the cutting assembly 10 by 90 degrees so that the longitudinally-extending portions 262 (FIG. 8) of the inner tube's two L-shaped slots 260 are aligned with the front plug's two locking pins 435 (FIG. 3), and so that the outer tube's two locking pins 160 (FIGS. 6 and 8) are realigned with the handle assembly's side slots 320, then depressing the gate assembly's top button 350 (FIGS. 3, 6 and 8) so as to re-align gate slots 370 (FIG. 8) with handle slots 320 (FIGS. 4 and 6), and finally withdrawing cutting assembly 10 from handle assembly 15.

Morcellator 5 is used as follows. First, the distal end of the morcellator is placed next to a relatively large tissue mass which is to be dissected. This is done while spring 485 holds inner tube 200 in its distal-most position, so that the outer tube's distal window 120 is closed and so that the morcellator's handle members 405 are in their inboard position (FIGS. 1 and 2). Then handle members 405 are pulled apart so as to draw inner tube 200 rearwardly, against the force of spring 485, and so as to open up the outer tube's rectangular distal opening 120 (FIGS. 3, 6 and 7). Next, morcellator 5 is moved against the tissue mass so that a portion of the tissue mass enters morcellator opening 120. Handle members 405 are then urged together again so as to drive inner tube 200 forward, thereby closing the outer tube's window 120. As this occurs, the cutting assembly's sharp edges 125 (FIGS. 3, 6 and 7) and 225 (FIG. 7) confront one another and thereby sever a piece of tissue off of the relatively large tissue mass. This severed piece of tissue will be contained within the distal end of inner tube 200. Handle members 405 are urged all the way together (FIG. 1) so that inner tube 200 bottoms out in annular groove 130. As this occurs, the severed piece of tissue contained within inner tube 200 will engage the outer tube's cylindrical plug 140 and be moved proximally by this engagement until the severed piece of tissue engages the inner tube's tissue barbs 250. Next, handle members 405 are forced apart again, thereby causing inner tube 200 to move proximally once more. This will in turn cause the severed piece of tissue contained within the inner tube to be impaled on the inner tube's distally-facing barbs 250 and then to be carried proximally with the retreating inner tube. As inner tube 200 moves proximally within the stationary outer tube, the impaled piece of tissue next engages the outer tube's own barbs 150. Handle members 405 are moved apart until pins 475 and 480 (FIG. 3) reach the limit of their travel within camming slots 420 (FIG. 3). At this point the outer tube's rectangular opening 120 will be completely opened up again (FIGS. 3, 6 and 7), and the severed piece of tissue will reside on the proximal side of the outer tube's rectangular opening 120, in engagement with both the inner tube's barb members 250 and the outer tube's barb members 150. Thereafter, another piece of tissue may be severed from the tissue mass, by first moving the morcellator against the tissue mass so that another portion of the tissue mass enters morcellator opening 120, and then urging handle members 405 together again so as to drive inner tube 200 proximally so as to close the outer tube's distal opening 120 and thereby cut off another piece of tissue. In this respect it should be appreciated that as inner tube 200 moves proximally to shear off this second piece of tissue, the previously sheared piece of tissue will be impaled on the outer tube's distally facing barbs 150 and thus held against any movement distally with the advancing inner tube 200. As the inner tube moves further distally, the severed piece of tissue will slip off the inner tube's barbs 250 and remain impaled on the outer tube's barbs 150. In this way it will be seen that barbs 150 and 250 together allow severed pieces of tissue to progress proximally down cutting assembly 10 towards handle assembly 15, but prevent the severed tissue from moving distally again with the reciprocating inner tube 200. Subsequent pieces of tissue may be sheared off a tissue mass by repeating the foregoing procedure.

Thus it will be seen that morcellator 5 may be used to dissect a relatively large tissue mass by progressively shearing off small pieces of the tissue mass with the morcellator, with these small pieces of tissue progressing serially down the interior of cutting assembly 10. These severed pieces of tissue may be observed by the surgeon while they are still in the morcellator, due to the transparent nature of plastic shaft portion 170 (FIG. 3) and 270 (FIG. 3). Furthermore, these pieces of tissue may be easily transported to pathology for biopsy studies simply by detaching cutting assembly 10 from handle assembly 15 in the manner previously described, and then forwarding the entire cutting assembly 10 to the lab along with its captivated tissue.

Looking next at FIGS. 9-22, tissue containment device 20 generally comprises a tissue containment assembly 25 and a handle assembly 30.

Tissue containment assembly 25 generally comprises a cylindrical body 505 (FIGS. 9, 11 and 14), a tissue containment means 510 (FIGS. 9, 10 and 14) and a cylindrical coupling 515 (FIGS. 9-11 and 14).

Figures 14, 14A:
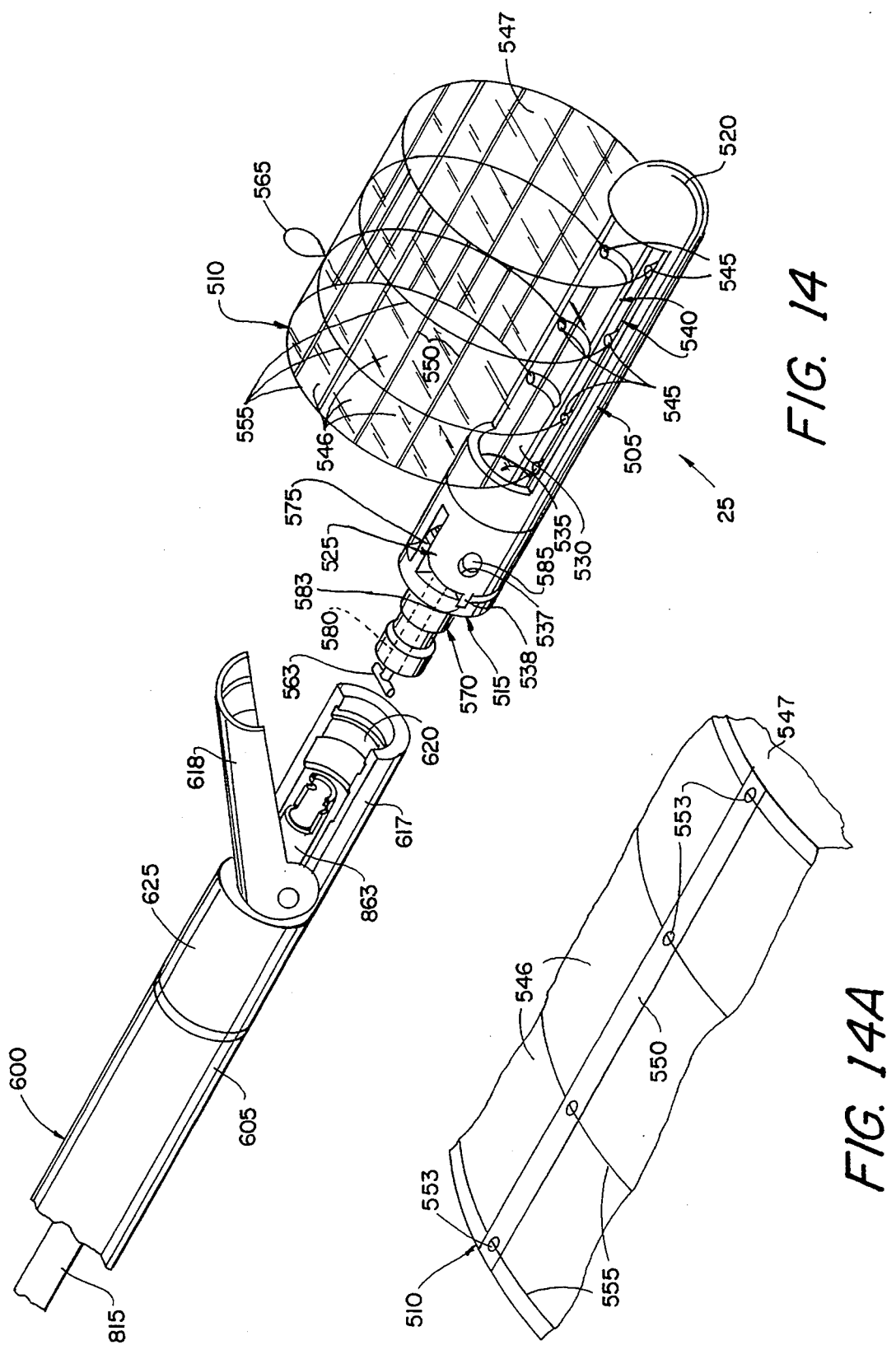
FIG. 14 is a view showing the distal end of the tissue containment device, with the device's tissue containment assembly being shown in telescoping relation to the distal end of the device's shaft.
FIG. 14A is a view showing a portion of the device's containment means.

Cylindrical body 505 generally comprises a rounded distal tip 520 (FIGS. 9-11 and 14), a bifurcated proximal end 525 (FIGS. 9-11 and 14), and a recessed portion 530 (FIGS. 11 and 14). An interior passageway 535 (FIG. 14) extends between the bifurcated proximal end 525 and recessed portion 530, whereby the interior of the recessed portion 530 can communicate with the region proximal to bifurcated proximal end 525. An oval-shaped opening 537 (FIGS. 9 and 14) extends across bifurcated proximal end 525, and a tongue 538 (FIGS. 9 and 14) extends proximally from one section of bifurcated proximal end 525. A pair of filament manifolds 540 (FIGS. 11 and 14) are disposed in the cylindrical body's recessed portion 530 and its interior passageway 535. Each manifold 540 comprises an open end 542 (FIG. 11) located in the cylindrical body's bifurcated proximal end 525 and a plurality of openings 545 (FIGS. 11 and 14) which are disposed along one side of recessed portion 530. Filament manifolds 540 essentially provide filament conduits between interior passageway 535 and manifold openings 545.

Tissue containment means 510 generally comprises a cylindrical bag or net or other containment element 546 (FIGS. 14 and 14A) which is closed off at its distal end by an end wall 547 (FIGS. 14 and 14A). The proximal end of the bag or net or other containment element 546 is open. The bag or net or other containment element 546 is flexible and may or may not be formed out of a material having some sort of memory characteristic whereby the bag will attempt to return to a generally cylindrical shape when so permitted. Tissue containment means 510 also comprises a plurality of longitudinally-extending, relatively rigid spars 550 (FIGS. 14 and 14A) which are securely attached to the side wall of the bag or net or other containment element 546. Each of the spars 550 has an opening 553 (FIG. 14A) formed therein. Tissue containment means 510 also comprises a plurality of closure filaments 555 (FIGS. 14 and 14A) terminating in pulling ends 560 (FIGS. 25-28). Closure filaments 555 pass through and slide easily within openings 553 formed in spars 550. Pulling ends 560 extend into manifold openings 545 (FIG. 14), pass through manifolds 540, through interior passageway 535 and are attached to a T-bar 563 (FIGS. 14 and 25-28) which is disposed proximally of cylindrical coupling 515. A deployment ring 565 (FIGS. 9, 10 and 11) is attached to one of the longitudinally-extending spars 550. Preferably deployment ring 565 is attached to the spar 550 which is diametrically-opposed to cylindrical body 505, so that it will be located on tissue containment means 510 at the furthest possible distance from cylindrical body 505. As a result of this construction, it will be seen that by pulling T-bar 563 in a proximal direction, tissue containment means 510 can be drawn into the cylindrical body's recessed portion 530 by the closure filaments 555 as they are retracted into filament manifolds 540. Alternatively, pulling outwardly on deployment ring 565 will cause tissue containment means 510 to be deployed out of the cylindrical body's recessed portion 530.

Cylinder coupling 515 (FIGS. 9-11 and 14) comprises a stepped outer profile 570 (FIG. 14), a distal tongue 575 (FIGS. 10 and 14), an interior passageway 580 (FIGS. 14 and 25), and a groove 583 (FIG. 14). Distal tongue 575 is sized so as to fit between the bifurcated proximal end 525 of cylindrical body 505, with a connecting pin 585 (FIGS. 9 and 14) extending through the opening 537 and a corresponding opening (not shown) formed in tongue 575 so as to pivotally connect cylinder coupling 515 to cylindrical body 505. By forming opening 537 with an oval shape and by providing tongue 538 and groove 583, cylindrical body 505 can be locked into longitudinal alignment with cylinder coupling 515 by aligning tongue 538 and groove 583 and then pressing cylindrical body 505 proximally against cylinder coupling 515. At the same time, cylindrical body 505 can be pivoted relative to cylinder coupling 515 simply by pulling cylindrical body 505 distally away from cylinder coupling 515 so that tongue 538 is withdrawn from groove 583.

Figure 15:
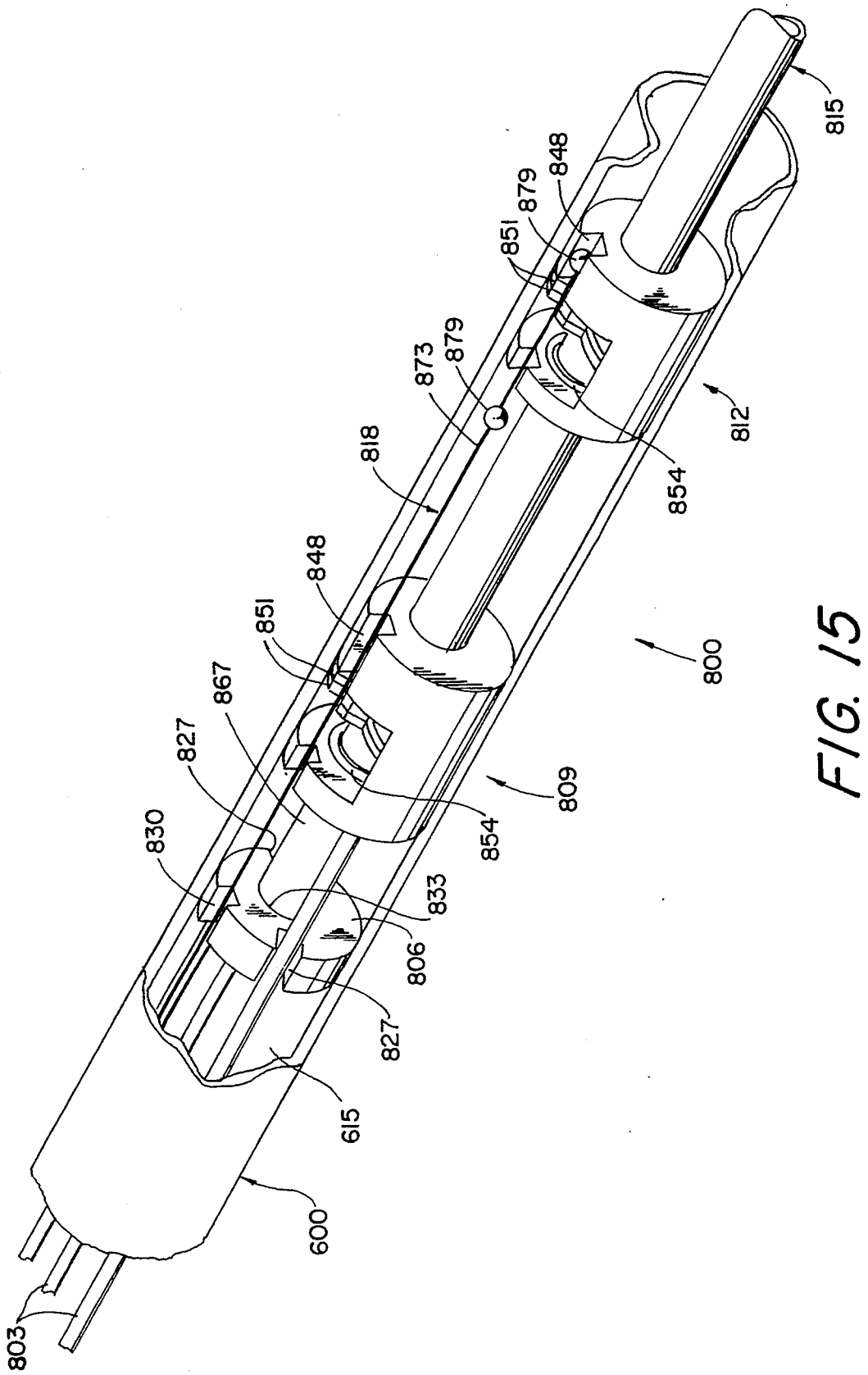
FIG. 15 is an enlarged view showing selected portions of the tissue containment device's retracting assembly.
Figure 16:
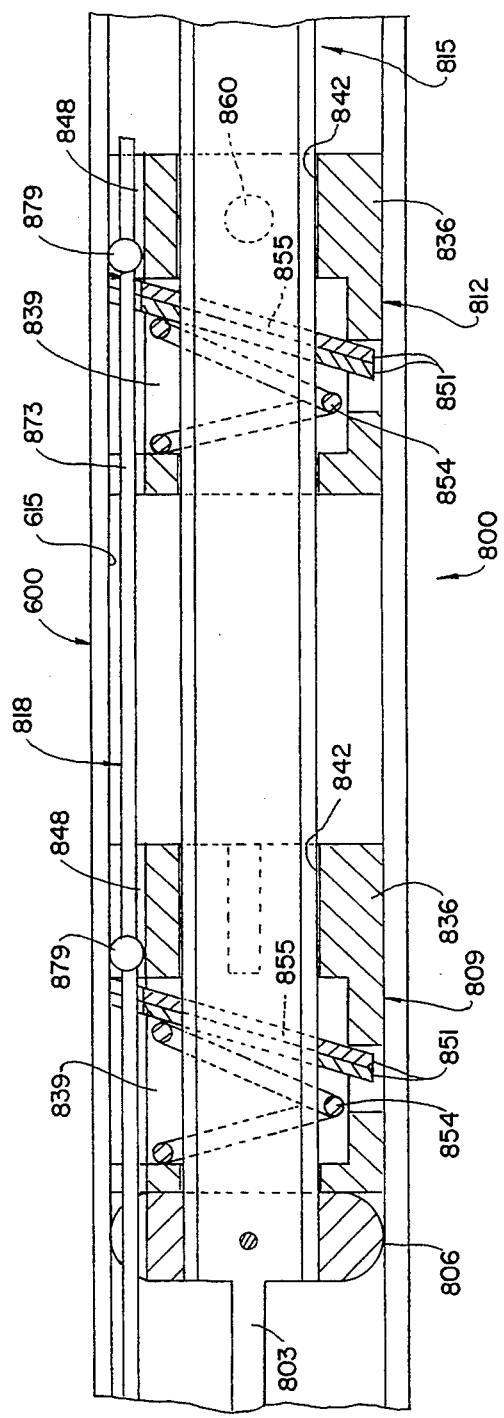
FIG. 16 is a side view in section of selected portions of the tissue containment device's retracting assembly.

Handle assembly 30 generally comprises a shaft 600 (FIGS. 9-11, 14 and 15-17), a handle body 700 (FIGS. 9-13) and a retracting assembly 800 (FIGS. 11, 15 and 16).

Shaft 600 generally comprises a distal end 605 (FIGS. 9-11 and 14), a proximal end 610 (FIGS. 9-11), and an interior opening 615 (FIGS. 11 and 15-17). The distal end 605 of shaft 600 is configured so as to have a fixed lower portion 617 (FIG. 14) and a hinged upper portion 618 (FIG. 14). A plurality of counterbores 620 (FIG. 14) are formed in the distal end of the shaft when fixed lower portion 617 and hinged upper portion 618 are united. A sliding sleeve 625 (FIG. 14) is disposed about the distal end of shaft 600. Sleeve 625 is adapted to cover or uncover the shaft's hinged upper portion 618, whereby hinged upper portion 618 may be held fast against fixed lower portion 617 or released so as to be able to pivot away from fixed lower portion 617. Counterbores 620 are arranged so as to have a profile corresponding to the stepped outer profile 570 (FIG. 14) of cylinder coupling 515, whereby sleeve 625 can be slid back, hinged upper portion 618 pivoted away from fixed lower portion 617, cylinder coupling 515 placed against fixed lower portion 617 so that counterbores 620 and stepped outer profile 570 mate, upper portion 618 swung back into engagement with fixed lower portion 617, and sleeve 625 slid forward again so as to lock cylinder coupling 515 securely to shaft 600, while still allowing full rotational movement of cylinder coupling 515 relative to the shaft.

Shaft 600 also comprises a proximal opening 630 (FIG. 11).

The proximal end 610 of shaft 600 is fixed to handle body 700. More particularly, and looking now at FIG. 11, handle body 700 generally comprises a housing 705 having a central bore 710 terminating in an end wall 715. A top recess 720 is formed in the top side of housing 705. First and second vertical openings 725 and 730 connect top recess 720 with central bore 710 and the interior of shaft 605, respectively. A trigger 735 (FIGS. 9-13) is pinned to housing 705 by means of a pin 740. A piston 745, having a distal end surface 750 and a proximal end surface 755, is slidably disposed in central bore 710.

A linkage assembly 760 connects trigger 735 to piston 745. More particularly, linkage assembly 760 comprises a first link 765 and a second link 770. A pin 775 connects link 765 to trigger 735. A pin 780 connects link 765 to link 770. A pin 785 connects link 770 to piston 745. A spring 790 is disposed between end wall 715 and the piston's proximal end surface 755. As a result of this construction, spring 790 will normally bias piston 745 distally and trigger 735 upwards, away from housing 705. However, it will also be appreciated that when trigger 735 is pressed downward, linkage assembly 760 will force piston 745 to move proximally against the force of spring 790.

Handle assembly 700 also comprises a release button 793 (FIGS. 9-11) having a proximal end 794 (FIG. 11) and a spring 795 (FIG. 11). Release button 793 is pivotally connected to handle body 700 by a pivot pin 797 (FIG. 11). Spring 795 normally biases release button 793 upwards, and proximal end 794 distally, as will hereinafter be discussed in further detail. Retracting assembly 800 generally comprises a pair of piston rods 803 (FIGS. 11 and 15-17), a guide ring 806 (FIGS. 15-17), an advancing mechanism 809 (FIGS. 15-17), a holding mechanism 812 (FIGS. 15 and 16), a connecting rod 815 (FIGS. 11 and 14-17), and a release rod 818 (FIGS. 11 and 15-17).

Piston rods 803 each comprise a distal end 821 (FIG. 17) and a proximal end 824 (FIG. 11). Piston rods 803 are connected at their distal ends to advancing mechanism 809, and at their proximal ends to piston 745. Thus it will be seen that as piston 745 reciprocates back and forth within bore 710 under the influence of trigger 735 and spring 790, advancing mechanism 809 will be correspondingly moved back and forth within shaft 600.

Guide ring 806 is a disk-like device fixed in place within shaft 600. Guide ring 806 comprises a pair of side notches 827 (FIG. 15), a top notch 830 (FIGS. 15 and 17), and a central opening 833 (FIG. 15). Side notches 827 accommodate and help stablize piston rods 803 as they move back and forth within shaft 600. Top notch 830 accommodates and helps stablize release rod 818 as it also moves back and forth within shaft 600, as will hereinafter be described in further detail. The guide ring's central opening 833 accommodates and helps stabilize connecting rod 815 as the connecting rod is advanced toward the proximal end of tissue containment device 20, as will hereinafter be described in further detail.

Figure 22:
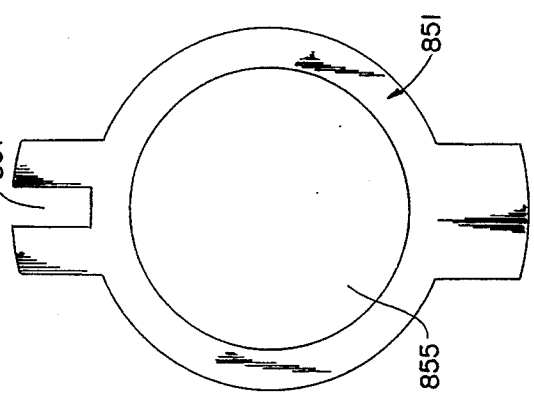
FIG. 22 is an end view of one of the gripper elements employed in the tissue containment device's retracting assembly.

Advancing mechanism 809 (FIGS. 11 and 15-17) and holding mechanism 812 (FIGS. 11, 15 and 16) are substantially identical to one another, except that advancing mechanism 809 is attached to piston rods 803 and reciprocates back and forth within shaft 600, whereas holding mechanism 812 is fixedly attached to the interior of shaft 600. Advancing mechanism 809 and holding mechanism 812 each generally comprise a body 836 (FIGS. 16-21) having a central cavity 839 (FIGS. 16-20), a central opening 842 (FIGS. 16, 17 and 21), and a top groove 848 (FIGS. 15-17 and 21). A plurality of grippers 851 (FIGS. 15-17 and 22) and a spring 854 (FIGS. 15-17) are disposed in each body 836. Each gripper 851 includes a central opening 855 (FIGS. 16 and 22) and a top slot 857 (FIG. 22). The distal ends of piston rods 803 are screwed into a pair of threaded bores 858 (FIGS. 17-21) formed in the body 836 of advancing mechanism 809. A locking pin 860 (FIG. 16) locks the body 836 of locking mechanism 809 to shaft 600.

Springs 854 (FIGS. 15-17) in advancing mechanism 809 and holding mechanism 812 normally bias their associated grippers 851 into an inclined position (FIGS. 15-17) so that the grippers bind with and thereby securely grip connecting rod 815. At the same time, however, grippers 851 can also overcome the bias of springs 854 so as to assume a substantially vertical position, in which case connecting rod 815 can pass cleanly through the central openings 855 of the grippers. On account of this construction, when piston rods 803 are moved proximally within shaft 600 by a retreating piston 745, thereby causing advancing mechanism 809 to also move proximally within shaft 600, the advancing mechanism's grippers 851 will engage connecting rod 815 and pull it proximally within the shaft along with connecting mechanism 809. As this occurs, the grippers 851 within the stationary holding mechanism 812 will pivot within their associated body 836 so as to assume a vertical position and thereby allow the shaft to move proximally relative to the stationary holding mechanism 812. In a corresponding manner, when piston rods 803 are moved distally within shaft 600 by an advancing piston 745, thereby causing advancing mechanism 809 to also move distally within shaft 600, the grippers 851 within the stationary holding mechanism 812 will bind with connecting rod 815 so as to prevent the connecting rod from moving distally within shaft 600. As this occurs, the grippers 851 within the advancing mechanism 809 will assume a vertical position so as to permit the advancing mechanism's body 836 to move distally relative to the connecting rod 815 which has been stabilized in position by the stationary holding mechanism 812. In this way it will be seen that advancing mechanism 809 and holding mechanism 812 can coact so as to permit connecting rod 815 to be incrementally moved proximally toward handle body 700 as piston 745 reciprocates back and forth within housing 705, yet will normally prevent connecting rod 815 from moving distally away from handle body 700 as piston 745 reciprocates within housing 705.

Connecting rod 815 itself comprises a distal end 863 (FIG. 14) and a proximal end 867 (FIG. 15). Distal end 863 includes a cut away profile that is adapted to grasp the tissue containment assembly's T-bar 563. In this way it will be seen that as connecting rod 815 is moved proximally within shaft 600 by the reciprocating piston 745 and retracting assembly 800, T-bar 563 will be drawn proximally as well so as to retract tissue containment means 510 into recessed portion 530 of cylindrical body 505.

Figure 17:
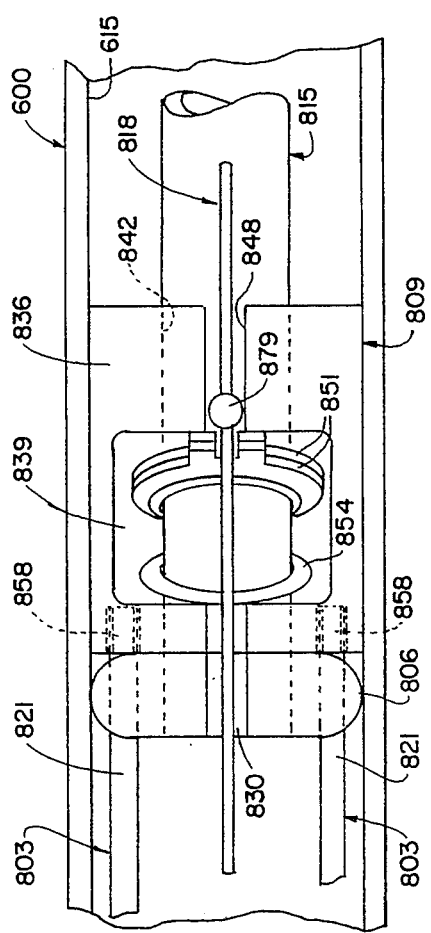
FIG. 17 is a top view of selected portions of the tissue containment device's retracting assembly.
Figure 20:
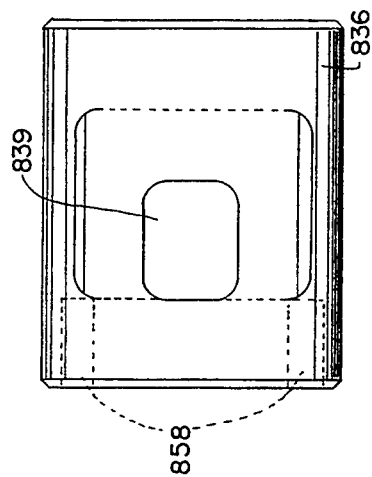
FIG. 20 is a bottom view of the same element shown in FIGS. 18 and 19.
Figure 18:
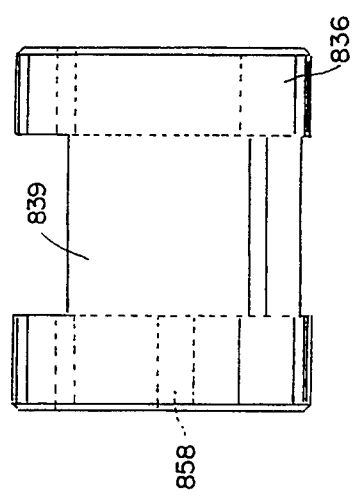
FIG. 18 is a side view of one of the elements utilized in the tissue containment device's retracting assembly.
Figure 19:
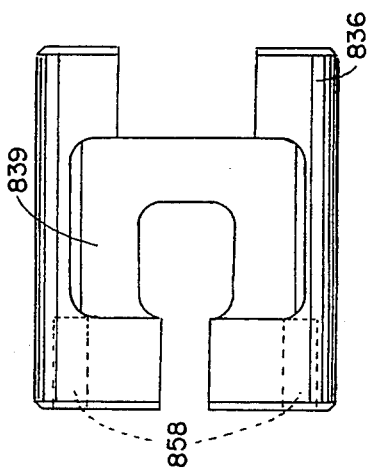
FIG. 19 is a top view of the same element shown in FIG. 18.
Figure 21:
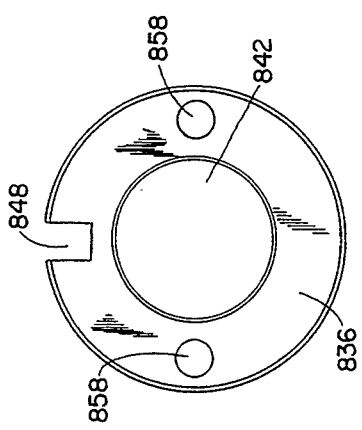
FIG. 21 is an end view of the proximal end of the same element shown in FIGS. 18–20.

Retracting assembly 800 also comprises a release rod 818 (FIGS. 11 and 15-17). Release rod 818 comprises a distal end 873 (FIGS. 15 and 16), a proximal end 876 (FIG. 11), and a plurality of release means 879 (FIGS. 15-17). The proximal end of release rod 818 is connected to the proximal end 794 of release button 793 so that release rod 818 will be moved proximally when relase button 793 is depressed. Release rod 818 passes through the guide ring's top notch 830 (FIGS. 15 and 17) and the top slots 857 in grippers 851 of advancing mechanism 809 and holding mechanism 812. Release means 879 preferably take the form of circular or disklike enlargements placed along the length of release rod 818. Release means 879 are disposed on release rod 818 so that they will normally lie on the distal side of grippers 851 in advancing mechanism 809 and holding mechanism 812. However, by depressing button 793, release rod 818 may be forced to move in a proximal direction whereby release means 879 will engage and force grippers 851 into a vertical orientation. Thus it will be seen that by depressing release button 793, both the advancing mechanism 809 and the holding mechanism 812 may be forced to release the hold that at least one of them will normally exert on connecting rod 815 so as to permit connecting rod 815 to be moved distally.

As a result of the foregoing construction, it will be seen that by simultaneously depressing release button 793 and pulling outward on deployment ring 565, tissue containment means 510 may be deployed out of the cylindrical body's recessed portion 530. At the same time, however, repeated pulling on trigger 735 will cause the retracting assembly 800 to progressively draw T-bar 563 in a proximal direction, whereby tissue containment means 510 will be retracted back into recessed portion 530 of cylindrical body 505.

Tissue containment device 20 is used as follows. First the device has its tissue containment means 510 fully retracted into the recessed portion 530 of cylindrical body 505. Then the distal end of device 20 is placed close to the tissue mass which is to be captured by the device. Next, release button 793 is depressed and another tool (such as, for example, the front knob 145 of the morcellator 5 previously disclosed) is used to pull tissue containment means 510 from device 20 using deployment ring 565. Then tissue containment device 20 and/or the tissue mass is/are manipulated so as to position the tissue mass into the tissue containment means 510. Next, trigger 735 is repeatedly depressed so as to retract the tissue containment means 510 back into cylindrical body 505 and thereby securely capture the tissue mass to device 20. Trigger 735 may thereafter be further depressed as required so as to keep the tissue mass securely captured to tissue containment device 20. FIGS. 23–28 show morcellator 5 and tissue containment device 20 dissecting a mass of tissue 1000 in accordance with the present invention.

Figure 23:
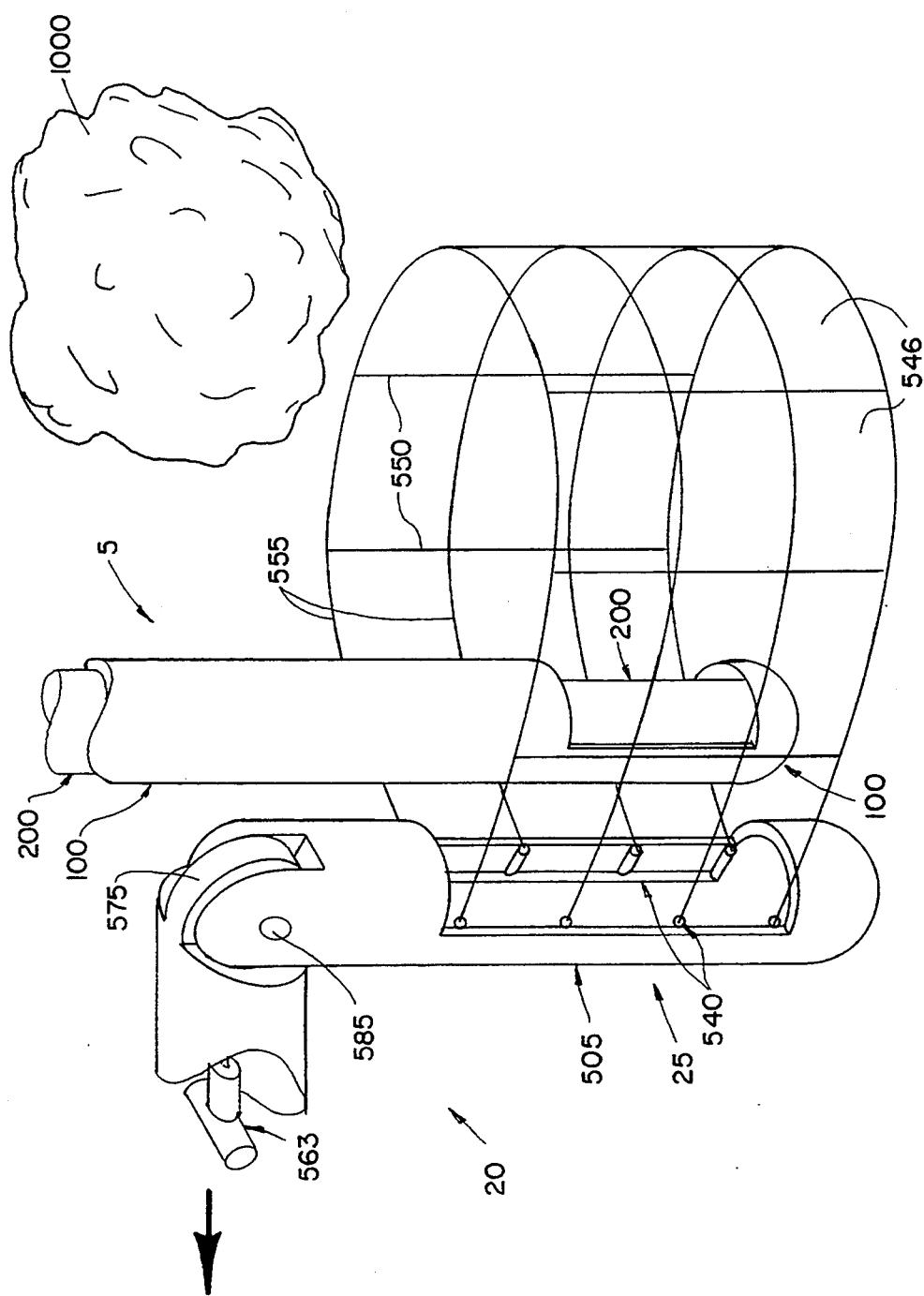
FIG. 23–28 are a series of views showing the morcellator and the aforementioned tissue containment device capturing and then dissecting a relatively large piece of tissue within the body.

More particularly, and looking now at FIG. 23, the distal end of a tissue containment device 20 is shown wherein the device's cylindrical body 505 is disposed at approximately a 90° angle relative to the remainder of device. This configuration can be desirable in some circumstances since it allows the device's cylindrical body 505 to be oriented substantially parallel to the morcellator's distal end 105, while still permitting the handle elements of the two tools to be disposed at right angles to one another. In FIG. 23, containment means 510 have been fully extracted from the cylindrical body's recessed portion 530, and the morcellator's distal end 105 has been placed therein. Tissue mass 1000 is shown adjacent to the open proximal end of containment means 510, ready to be captured therein.

Figure 24:
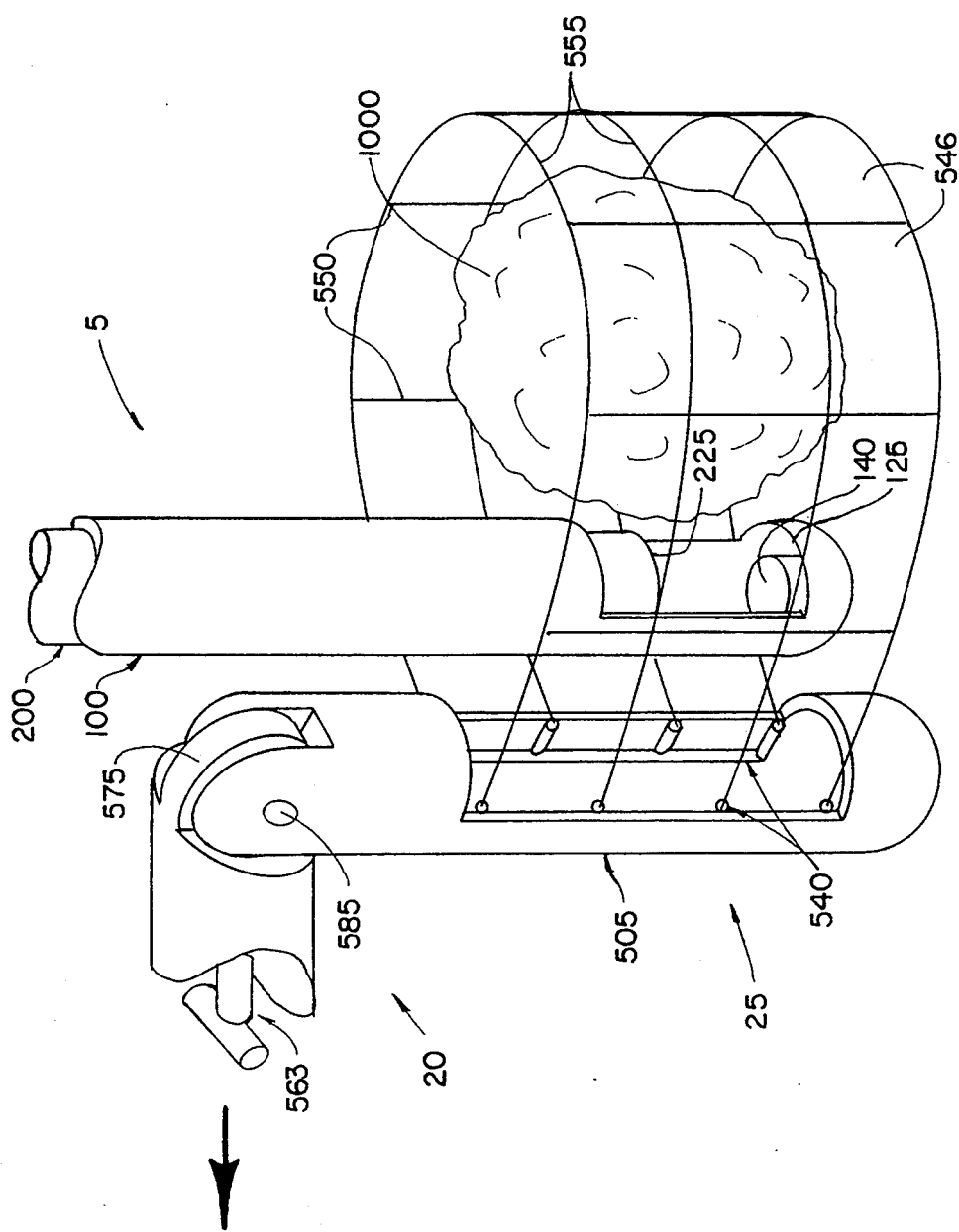
Figure 25:
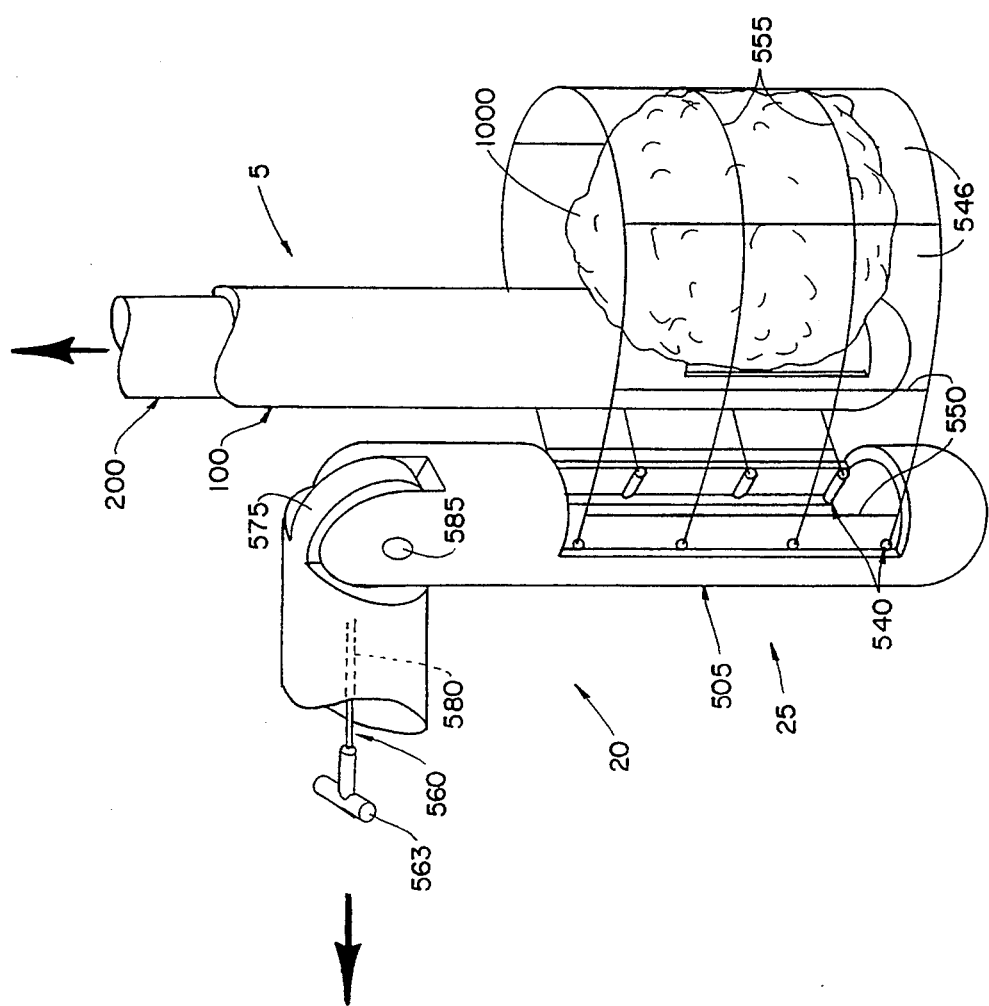

Next, and looking now at FIG. 24, tissue mass 1000 has been manipulated into containment means 510 and the morcellator has had its distal end opening 120 partially opened so as to expose the morcellator's sharp cutting edges 125 and 225. Then the surgeon will repeatedly actuate the tissue containment device's trigger 735 so as to draw connecting rod 815 proximally and hence retract containment means 510 into the cylindrical body's recessed portion 530. This is done so as to securely capture tissue mass 1000 to the two tools, in the manner illustrated in FIG. 25.

Figure 26:
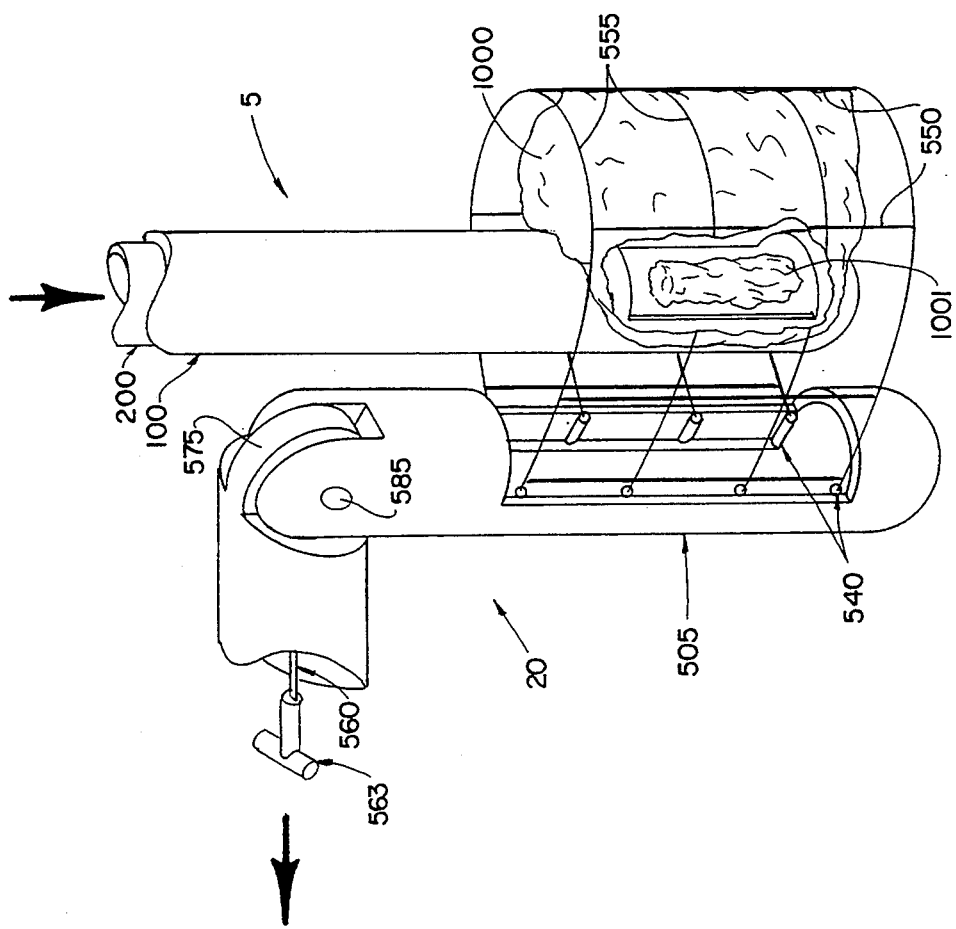
Figure 27:
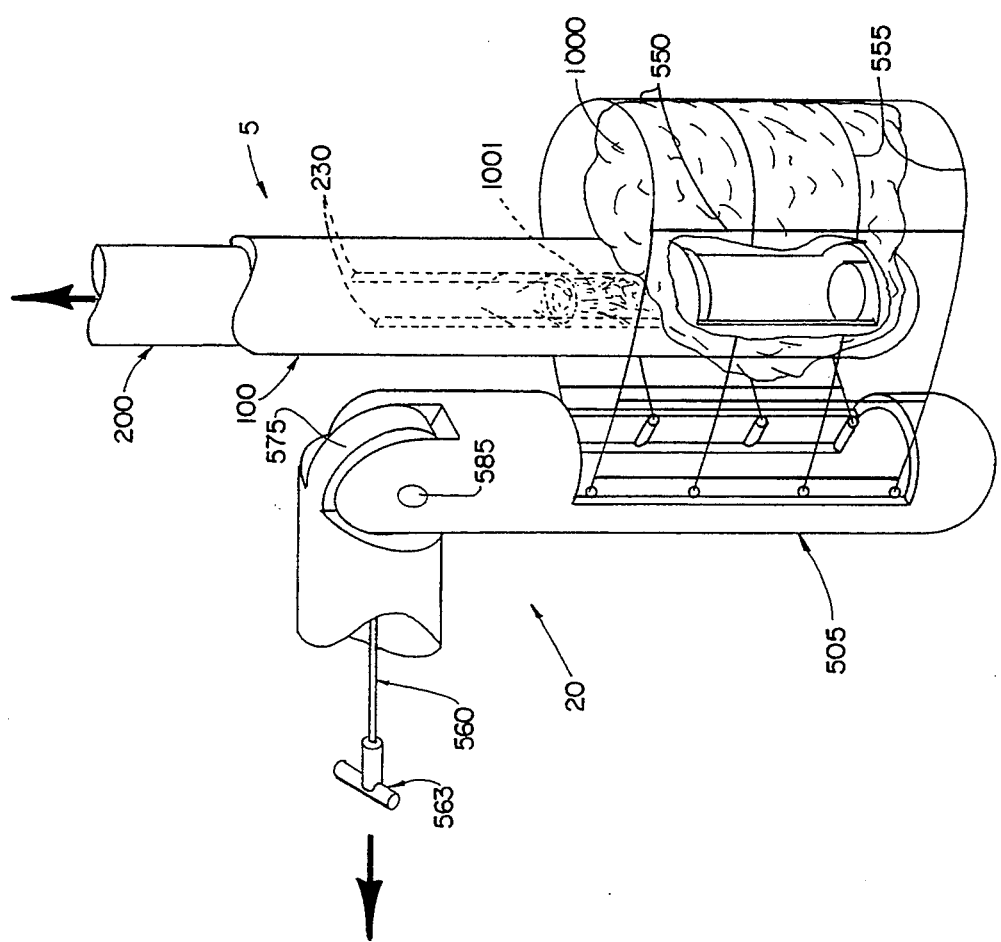

As tissue mass 1000 is securely captured within tissue containment means 510, a portion of the tissue mass will protrude into the morcellator's distal end opening 120. The surgeon can then squeeze morcellator handle members 405 together so as to close morcellator opening 120 and thereby sever a tissue portion 1001 from tissue mass 1000, as illustrated in FIG. 26. This tissue portion 1001 will reside within inner tube 200 in the manner previously described.

When handle members 405 are thereafter pulled apart again by the surgeon, inner tube 200 will be drawn proximally, and tissue portion 1001 will be impaled on the inner tube's barbs 250. Tissue portion 1001 will then be drawn proximally with inner tube 200 until the tissue portion comes into engagement with the outer tube's barbs 150, which protrude through the two diametrically-opposed, longitudinally-extending inner tube slots 230, seen in FIG. 27. The outer tube's barbs will thereafter prevent tissue portion 1001 from returning to opening 120 with inner tube 200 when the surgeon next squeezes handle members 405.

Figure 28:
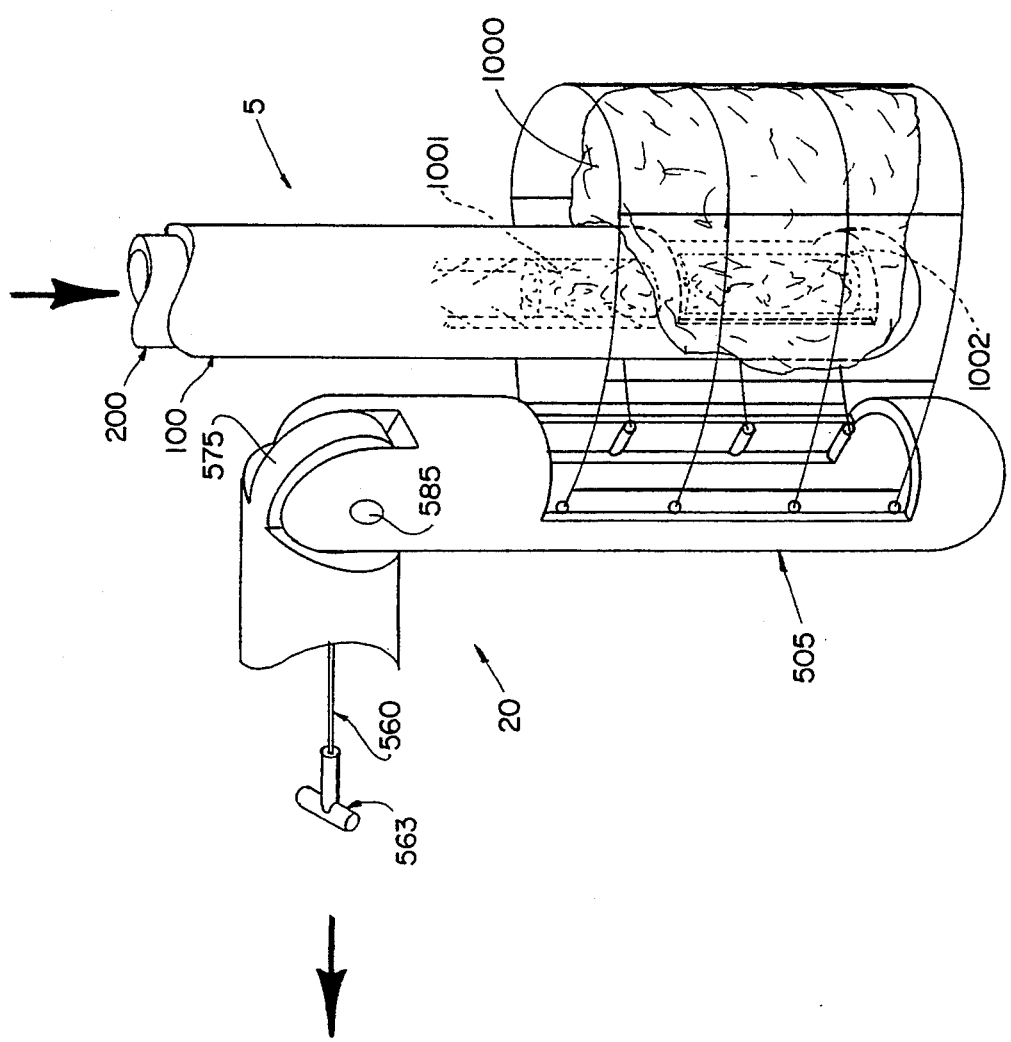

To sever another portion of tissue mass 1000, the surgeon depresses trigger 735 of tissue containment device 20 so as to further draw tissue mass 1000 into engagement with the morcellator's distal opening 120. This will cause a second tissue portion 1002 to protrude into distal opening 120. The surgeon then again squeezes handle members 405, thus driving inner tube 200 distally so as to sever tissue portion 1002 from tissue mass 1000, as seen in FIG. 28. Tissue portion 1002 is thereafter impaled on inner tube barbs 250, and thereafter drawn proximally into engagement with barbs 150 and tissue portion 1001, when inner tube 200 is moved proximally again. As this occurs, tissue portion 1002 pushes tissue portion 1001 further proximally and hence deeper into inner tube interior passageway 215. The foregoing process is then repeated as necessary until tissue mass 1000 is reduced to a desired size, or is dissected altogether.

What is claimed is:
1. A tissue containment device comprising:
   a shaft having a distal end, a proximal end, and an interior passageway extending between said distal end and said proximal end;
   a cylindrical body releasably connected to said distal end of said shaft, said cylindrical body comprising a distal end, a proximal end and an interior passageway extending between said distal end and said proximal end of said cylindrical body, and further comprising at least one manifold located within said cylindrical body's interior passageway, said manifold being adapted to guide closure means;
   containment means deployable from said cylindrical body, said containment means comprising a flexible, generally cylindrical containment element, at least one substantially rigid, longitudinally-extending spar connected to said flexible, generally cylindrical containment element, a plurality of openings formed in said spar, and closure means extending out of each at least one manifold and through said plurality of openings formed in said spar;
   a handle assembly;
   release means for permitting said containment means to be moved from (1) a first fully retracted position wherein said containment element is substantially fully withdrawn into said cylindrical body's interior passageway, and (2) a second fully deployed position wherein said containment element is substantially fully extended out of said cylindrical body's interior passageway; and retracting means connected to said closure means and adapted to move said containment means from said aforementioned second fully deployed position wherein said containment element is substantially fully extended out of said cylindrical body's interior passageway, to (3) a third intermediate position wherein said containment element is partially withdrawn into said cylindrical body's interior passageway, said retracting means being adapted to progressively retract said containment element further and further into said cylindrical body's interior passageway.

2. Apparatus according to claim 1 wherein said containment element comprises a cylindrical net having a closed off distal end and an open proximal end and further wherein said net comprises a plurality of closure filaments terminating in at least one pulling end.

3. Apparatus according to claim 2 comprising a pair of manifolds disposed in a recessed portion of said cylindrical body's interior passageway, said manifolds comprising an open end located in said proximal end of said cylindrical body and a plurality of openings disposed along at least one side of said recessed portion so as to provide filament conduits for said plurality of closure filaments.

4. Apparatus according to claim 3 comprising a plurality of longitudinally-extending rigid spars securely fastened to said net.

5. Apparatus according to claim 4 wherein said closure filaments slidably pass through said openings formed in said spars.

6. Apparatus according to claim 5 wherein said at least one pulling end extends through one of said manifolds and is operatively fastened to said retracting means.

7. Apparatus according to claim 6 wherein said net further comprises a deployment ring attached to at least one of said longitudinally-extending spars.

8. Apparatus according to claim 1 wherein said containment element comprises a cylindrical bag having a closed off distal end and an open proximal end.

9. Apparatus according to claim 1 wherein said cylindrical body is pivotally connected to a hinge positioned at said shaft's distal end.

10. Apparatus according to claim 9 wherein said handle assembly further comprises a sleeve slidably surrounding said shaft and adapted for covering said hinge.

11. Apparatus according to claim 10 wherein said handle assembly houses said retracting means.

12. Apparatus according to claim 11 wherein said retracting means comprise an advancing mechanism and a holding mechanism.

13. Apparatus according to claim 12 wherein said advancing mechanism and said holding mechanism are substantially identical to one another and further wherein said advancing mechanism is fastened to at least two piston rods so as to reciprocate back and forth within said shaft's interior passageway and said holding mechanism is fixably fastened to an interior surface of said shaft.

14. A morcellator system comprising a morcellator device in combination with a tissue containment device, said morcellator device comprising:

an outer tube having a distal end terminating in a distal end surface, a proximal end, an internal passageway extending between said distal end and said proximal end, and an opening formed in said distal end at a location proximal to said distal end surface and communicating with said internal passageway;

an inner tube having a distal end terminating in a distal end surface adapted for morcellating tissue, a proximal end, and an interior passageway extending between said distal end of said inner tube and said proximal end of said inner tube, with said inner tube being sized and disposed so as to make a close sliding fit within said outer tube;

a handle assembly comprising a body and actuating means, with said proximal end of said outer tube being attached to said body and with said proximal end of said inner tube being attached to said actuating means;

said actuating means being adapted to move said inner tube between (1) a first distal position wherein said opening formed in said distal end of said outer tube is closed off by said inner tube, and (2) a second proximal position wherein said opening formed in said distal end of said outer tube is at least part way open;

first tissue holding means connected to said inner tube and projecting into the interior passageway of said inner tube so as to permit tissue to move proximally through said inner tube and to prevent tissue from moving distally through said inner tube; and second tissue holding means connected to said outer tube and projecting into said interior passageway of said inner tube so as to permit tissue to move proximally through said outer tube and to prevent tissue from moving distally through said outer tube; and said tissue containment device comprising:

a shaft having a distal end, a proximal end, and an interior passageway extending between said distal end and said proximal end;

a cylindrical body releasably connected to said distal end of said shaft, said cylindrical body comprising a distal end, a proximal end and an interior passageway extending between said distal end and said proximal end of said cylindrical body, and further comprising at least one manifold located within said cylindrical body's interior passageway, said manifold being adapted to guide closure means;

containment means deployable from said cylindrical body, said containment means comprising a flexible, generally cylindrical containment element, at least one substantially rigid, longitudinally-extending spar connected to said flexible, generally cylindrical containment element, a plurality of openings formed in said spar, and closure means extending out of said at least one manifold and through said plurality of openings formed in said spar wherein said containment element is sized so as to receive both said tissue and said distal end of said outer tube of said morcellator device;

a handle assembly;

release means for permitting said containment means to be moved from (1) a first fully retracted position wherein said containment element is substantially fully withdrawn into said cylindrical body's interior passageway, and (2) a second fully deployed position wherein said containment element is substantially fully extended out of said cylindrical body's interior passageway; and retracting means connected to said closure means and adapted to move said containment means from said aforementioned second fully deployed position wherein said containment element is substantially fully extended out of said cylindrical body's interior passageway, to (3) a third intermediate position wherein said containment element is partially withdrawn into said cylindrical body's interior passageway, said retracting means being adapted to progressively retract said containment element further and further into said cylindrical body's interior passageway.

15. Apparatus according to claim 14 wherein said containment element comprises a net with a deployment ring.

16. Apparatus according to claim 15 wherein said morcellator device comprises a knob disposed on said outer tube's distal end and adapted for engaging said deployment ring so as to deploy said containment element.

* * * * *